(12) United States Patent
Renner et al.

(10) Patent No.: US 10,467,438 B1
(45) Date of Patent: Nov. 5, 2019

(54) PROXIMITY SENSOR ALGORITHMS TO CONTROL TRANSMIT POWER OF A USER DEVICE AFTER WATER IMMERSION

(71) Applicant: Amazon Technologies, Inc., Seattle, WA (US)

(72) Inventors: Peter Eli Renner, Santa Clara, CA (US); Ruomeng Yu, Belmont, CA (US); Ming Zheng, Santa Clara, CA (US); Serkan Hatipoglu, Campbell, CA (US); Felix Liu, Milpitas, CA (US); Han Seob Choi, Mountain View, CA (US); Mudit Sunilkumar Khasgiwala, Milpitas, CA (US)

(73) Assignee: Amazon Technologies, Inc., Seattle, WA (US)

( * ) Notice: Subject to any disclaimer, the term of this patent is extended or adjusted under 35 U.S.C. 154(b) by 174 days.

(21) Appl. No.: 15/710,420

(22) Filed: Sep. 20, 2017

(51) Int. Cl.
*G06F 21/84* (2013.01)
*G06F 11/22* (2006.01)
*G01N 27/22* (2006.01)
*G01N 27/04* (2006.01)

(52) U.S. Cl.
CPC ........... *G06F 21/84* (2013.01); *G01N 27/048* (2013.01); *G01N 27/223* (2013.01); *G01N 27/227* (2013.01); *G06F 11/2221* (2013.01); *G06F 11/2284* (2013.01)

(58) Field of Classification Search
CPC .................................................... H04B 1/3838
See application file for complete search history.

(56) References Cited

U.S. PATENT DOCUMENTS

| 2012/0071195 | A1* | 3/2012 | Chakraborty | ........ H04B 1/3838 455/522 |
| 2015/0378496 | A1* | 12/2015 | Vandermeijden | ..... G06F 3/0416 345/174 |
| 2018/0358965 | A1* | 12/2018 | Rouaissia | ............. G06F 3/0418 |

* cited by examiner

*Primary Examiner* — Hsinchun Liao
(74) *Attorney, Agent, or Firm* — Lowenstein Sandler LLP

(57) ABSTRACT

Methods and systems are described for proximity condition detection of a recovery from sensor proximity saturation caused by water immersion of a user device. The device transmits data at a first transmit power level using an antenna. In one system, a proximity condition checker determines that a first proximity sensor and a second proximity sensor are saturated in an unknown state after a power event where the saturation caused at least in part by the presence of water in proximity to the first proximity sensor and the second proximity sensor. The proximity condition checker determines that 1) both the first proximity sensor and the second proximity sensor are no longer saturated and 2) water is no longer in proximity to the first proximity sensor and the second proximity sensor. In response, the user device can transmit data at an increased second transmit power level using the antenna.

20 Claims, 12 Drawing Sheets

PROXIMITY SENSOR ALGORITHMS TO CONTROL TRANSMIT POWER OF A USER DEVICE AFTER WATER IMMERSION

BACKGROUND

A large and growing population of users enjoys entertainment through the consumption of digital media items, such as music, movies, images, electronic books, and so on. Users employ various electronic devices to consume such media items. Among these electronic devices are electronic book readers, cellular telephones, personal digital assistants (PDAs), portable media players, tablet computers, netbooks, and the like. These electronic devices wirelessly communicate with a communications infrastructure to enable the consumption of the digital media items. Typically, the communications infrastructure dictates transmit power levels for the electronic devices to use when transmitting data to the communications infrastructure. Some electronic devices include transmit power managers for making their own determinations regarding what transmit power levels to use.

Some bodies of research suggest that radiation output by electronic devices during wireless transmission of data can cause damage to the human body when such radiation is absorbed. However, since electronic devices lack the ability to control their transmit power levels, such electronic devices cannot adjust their transmit power levels to reduce user exposure to radiation. This may also consequently cause these electronic devices to fail to comply with FCC regulations regarding the specific absorption rate (SAR) permitted by electronic devices. SAR is a measure of the rate at which energy is absorbed by the body when exposed to a radio frequency (RF) electromagnetic field. In addition, the user's body can block the RF electromagnetic field in the direction of the user's body, thus reducing the gain in that direction. This may also cause difficulty in meeting the SAR requirements since more power is required to offset the signal loss by the user's body.

BRIEF DESCRIPTION OF THE DRAWINGS

The present invention will be understood more fully from the detailed description given below and from the accompanying drawings of various embodiments of the present invention, which, however, should not be taken to limit the present invention to the specific embodiments, but are for explanation and understanding only.

DETAILED DESCRIPTION

Figure 1:
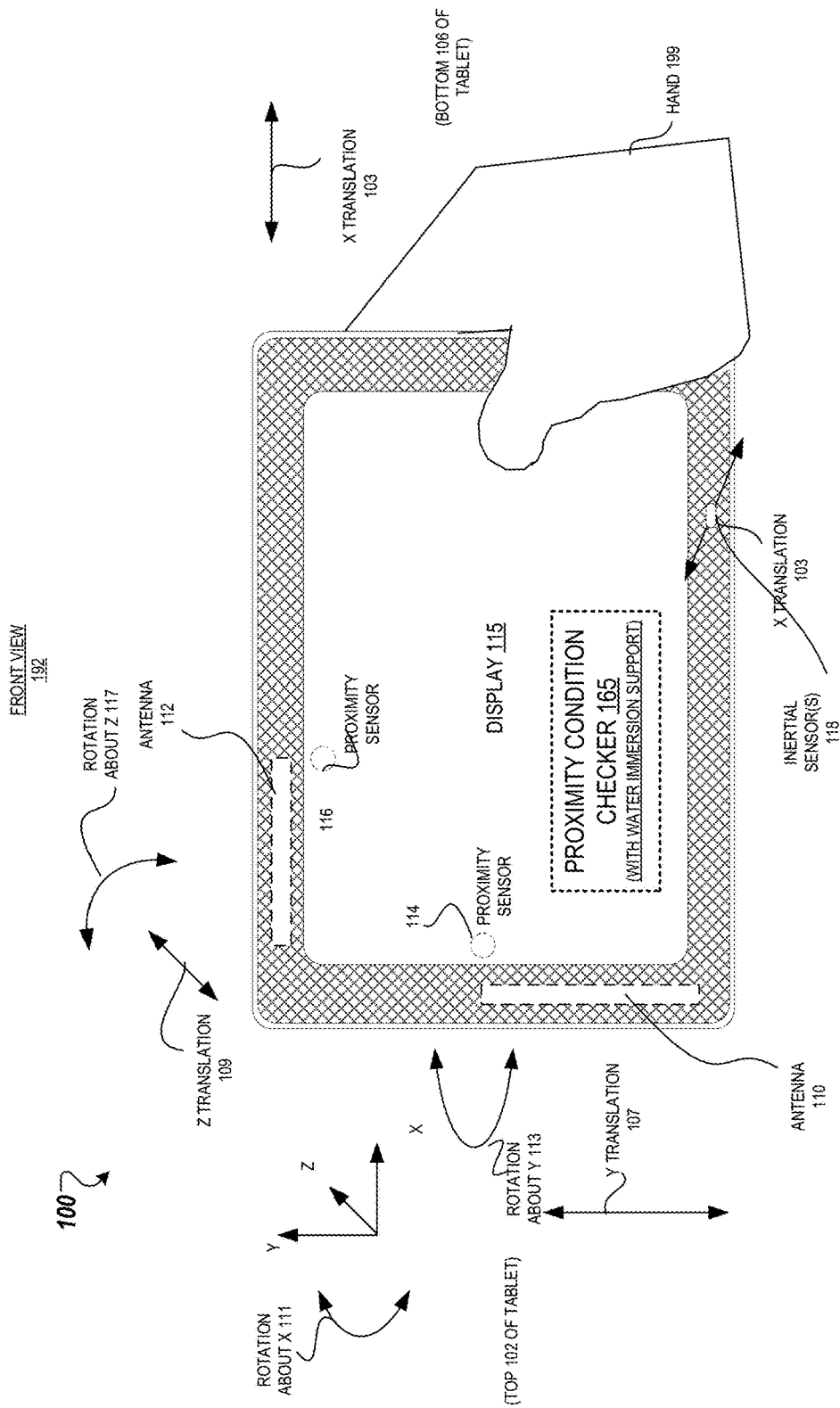
FIG. 1 illustrates a tablet computing device with a first antenna, a second antenna, a first proximity sensor, a second proximity sensor, an inertial sensor, and a proximity condition checker with water immersion support according to one embodiment.

Methods and systems are described for detecting recovery from temporary proximity sensor saturation caused by water using values of two or more proximity sensors located relative to at least one antenna of a user device. The user device can start in a reduced transmit power level until the user device determines that the proximity sensors are not in saturation caused by water, and can subsequently increase the transmit power level to be used by the antenna. A user device obtains values of the proximity electrodes (also referred to as proximity sensor pads), checks for trigger conditions, and instructs a transmit power manager to increase the transmit power level to transmit data when trigger conditions are met. The embodiments described herein are directed to complying with SAR requirements by decreasing a transmit power of an antenna when proximity-to-user conditions are met and when the user device powers up. In the event that the user device has been immersed or otherwise exposed to water, the user device can detect that the proximity sensors are saturated and recovery from being in saturation before permitting the transmit power to be increased. The user device may be any content rendering device that includes a wireless modem for connecting the user device to a network. Examples of such user devices include electronic book readers, cellular telephones, personal digital assistants (PDAs), portable media players, tablet computers, netbooks, and the like.

As SAR is dependent on the average power transmitted, by reducing the transmit power level when a human body part or an SAR phantom (used during the testing of the user device) (hereinafter referred to as phantom) is detected for the different proximity conditions, the average transmitted power can be reduced when the user device is in proximity to a person (e.g., a human body part or phantom) or a phantom. The embodiments described herein have the ability to detect when the user device is in proximity to a human body part or phantom for various proximity conditions and can reduce the transmit power level for SAR compliance. In addition, the embodiments described herein have the ability to detect when the user device is in an unknown state, caused at least in part by water, and the ability to detect when the user device is recovered from the unknown state.

In the consumer electronics world, FCC has a requirement of SAR in various conditions, such as 1.6 mW/g. For example, if the SAR limit of 1.6 mW/g cannot be met, the transmitted power by the user device needs to be reduced. The proximity sensor was introduced to detect the proximity of the human body. The proximity sensor is configured to detect proximity in various conditions that would exceed the SAR permitted set by the FCC if the device was transmitting at maximum power under those various conditions. As described herein, a proximity sensor can be used to check for proximity conditions as described herein. Once any one of the proximity conditions is met, a signal can be sent to a device system (e.g., a processor) to increase or reduce the transmitted power to meet FCC SAR requirement as described herein. For example, for a main antenna, the back off power may be 3 dB and 5 dB for GSM 1800 and WCDMA Band 1, respectively. For a diversity antenna, the back off power may be 5 dB for WCDMA Band 1 only. For the US AT&T SKU, no SAR power back off may be needed due to the FCC SAR waiver by use of Duty Factor, typically from 3 to 12%.

In other embodiments, the proximity sensor can be deployed to fulfill two functions: meet different regulatory bodies' SAR requirements by backing off RF power and to enhance the user experience by selecting an optimum antenna for different frequency bands, for example, GSM/WCDMA bands. Water immersion causes proximity sensor saturation temporarily. Although the proximity sensor may eventually recover to full functionality (e.g., 3-4 weeks), this may still violate a specified SAR specifications (e.g., non-US WAN devices) for the user device during the recovering period.

The embodiments described herein may be used to mitigate this potential issue. In one embodiment, a proximity sensor algorithm can accommodate for the potential proximity sensor saturation issues as described above. The proximity sensor algorithm may be implemented at very minimal customer impact. In one embodiment, the proximity sensor algorithm can send a triggering signal to a modem to back off its power if the proximity sensors are saturated because of water. Saturation is a state of the proximity sensor in which a signal that needs to be measured is larger than a measurement range of the sensor. The presence of water increases the signal (representative of the capacitance) measured by the proximity sensor and the proximity sensor is no longer able to reliably measure the capacitance in order to detect the presence of a human body part. One way this manifests is sensor readout. For example, in one instance, the sensor readout of 0xffffffff may indicate that the proximity sensor is saturated and hence cannot perform proximity detection reliably. The embodiments of the proximity sensor algorithm can work well in all conditions, even if the water immersion case, as long as the proximity sensors have not been re-calibrated after water immersions. However, if a user reboots the device, the device could enter a high transmitting power mode (or non-triggering), because, in the initial stage (at T0), the proximity differential reading is low due to the saturation. The proximity sensor performs a baseline calibration while being saturated. Consequently, there is no triggering event; potentially the SAR could be higher than a specified SAR specification.

In another embodiment, the proximity sensor algorithm can set a triggering state as a default in an initial modem (e.g., WAN modem) stage. If the device is switched on and the proximity sensor is saturated due to the water immersion, the proximity sensor algorithm can keep the initial triggering status until the proximity sensor recovers its functionality, such as illustrated and described herein. The proximity sensors' SAR trigger thresholds can be set comparatively low, e.g., typical value around 100, as compared to the proximity sensors' readings around 2000 when a user holds the device. Hence, as soon as the proximity sensor recovers its functionality, the normal triggering events take place as expected during other proximity sensor algorithms. This proximity sensor algorithm can ensure SAR compliance by guarantying that the SAR value will not exceed a SAR specification after the water immersion. A general response of a single proximity sensor is that raw data from the proximity sensor increases as an object (e.g., human body part or phantom) approaches the proximity sensor (i.e., as the distance between a proximity sensor pad and object decreases). Typically, a threshold is set for the proximity sensor, for example, set for a specific distance. The raw data or the difference of raw data is compared against the threshold and, once the threshold is met, the proximity sensor is triggered. FIGS. 1-3, 9-11 illustrate and describe devices and network in which the embodiments may be deployed. FIGS. 4, 5A, 5B, 7, and 8 illustrate various embodiments of a method that can implement the proximity sensor algorithms described above.

FIG. 1 illustrates a front view 192 of a tablet computing device 100 with a first antenna 110, a second antenna 112, a first proximity sensor 114, a second proximity sensor 116, an inertial sensor 118, and a proximity condition checker 165 with water immersion support according to one embodiment. The tablet computing device 100 has a display 115 and the tablet computing device 100 is illustrated in a landscape orientation with a top 102 of the tablet computing device 100 on the left of FIG. 1 and a bottom 106 of the tablet computing device 100 on the right of FIG. 1. The tablet computing device 100 is illustrated as being held by a hand 199 of a user. Although FIG. 1 illustrates a tablet computing device 100, in other embodiments, other electronic devices may be used in condition with the proximity condition checker 165, as described herein.

The first proximity sensor 114 and the second proximity sensor 116 can be separate circuits or circuits integrated into other circuits of the tablet computing device 100. The proximity sensor can include measurement circuits and a proximity sensor electrode (or sensor pad). For example, the proximity sensor may include a capacitance measurement circuit that measures the capacitance of one or more sensor electrodes to detect the presence of an object in proximity to the one or more sensor electrodes.

In one embodiment, a proximity sensor chip can be integrated with other circuits of the tablet computing device, such as a circuit board including one or more integrated circuits with various functionalities of the tablet computing device 100. For example, a processor can be one integrated circuit mounted on a circuit board and the proximity sensor can be another integrated circuit mounted on the same circuit board or a different circuit board. The proximity sensor can send a signal to the processor to indicate that any one of the proximity conditions is met based on the values of the proximity sensor pads. Alternatively, the proximity sensor chip can send raw data to the processor and the processor can determine whether any one of the proximity conditions is met using the techniques described herein. The processor may include a transceiver for the antenna and the processor controls the transmit power level to be used by the antenna. When the proximity sensor chip is in a triggered state, the processor reduces a transmit power level via the transceiver. Alternatively, the triggered state can control the reduction of the transmit power level using other mechanisms as would be appreciated.

In one embodiment, the first proximity sensor 114 and the second proximity sensor 116 can be implemented as two separate single electrodes (or an intersection between two electrodes the proximity sensor) coupled to a measurement circuit (or two separate measurements circuit). The measurement circuit measures a capacitance on the single electrode with respect to ground (or a mutual capacitance between an intersection of two electrodes) and converts the measured capacitance to a digital value, referred to as a raw count. The raw counts can be compared against one or more thresholds to detect an object in proximity to the electrode (or pair of electrodes). In one embodiment, two proximity sensor chips (integrated circuits) (not illustrated) and two proximity sensor pads may be used to implement the first proximity sensor 114 and the second proximity sensor 116. Each proximity sensor pad can be optimized separately based on the respective location on or within the tablet computing device 100. In one embodiment, the first proximity sensor 114 has a proximity sensor circuit (i.e., measurement circuit) and a first proximity electrode located at a location near the first antenna 110. The electrodes may be disposed inside a cover or on a surface of the cover of the tablet computing device 100. In one embodiment, the proximity sensor circuit may store the raw counts in memory to be read by the proximity condition checker 165. In another embodiment, the proximity condition checker 165 requests measurements be taken by the first proximity sensor 114 to obtain the values of the first proximity sensor. In another embodiment, a single proximity sensor circuit measures values corresponding to the two electrodes, represented in FIG. 1 as the two proximity sensors 114, 116. The proximity condition checker 165 can use the values of (measurements taken by) the proximity sensor circuit to determine whether any one of multiple conditions is met. The conditions may be defined by one or more different combinations of thresholds as described herein. The different thresholds can define different distances of the object relative to the antenna(s). The proximity condition checker 165 instructs a transceiver to increase the transmit power level to an increased transmit power level to transmit the data when certain conditions are met, as described herein. The proximity condition checker 165 can also instruct the transceiver to reduce the transmit power level to a reduced transmit power level when the conditions indicate the presence of water, the presence of an object, or the like. If these certain conditions are met, the proximity condition checker 165 is in a triggered state and can send a signal to a transceiver or a signal to a processing component that controls the transceiver. The signal can be an input to a transmit power manager executing on the user device. The input can designate a state of the proximity sensor of whether any of the proximity conditions are met. The signal can be maintained (or the triggered state) until none of the proximity conditions are met. A new signal, or a state of the same signal, can be changed to indicate that the proximity sensor is in an untriggered state when none of the proximity conditions are met.

In the depicted embodiment, the first proximity sensor 114 is disposed at a location closer in proximity to the first antenna 110 than the second antenna 112 and the second proximity sensor 116 is disposed closer in proximity to the second antenna 112 than the first antenna 110. The locations and numbers of proximity sensors may vary and may serve as different inputs to the proximity condition checker 165. For example, if additional antennas are included in the tablet computing device 100, the tablet computing device 100 could include additional proximity sensors. In one embodiment, the first proximity sensor 114 is located at a first edge of the first antenna 110 and the second proximity sensor 116 is located at a first edge of the second antenna 112. Alternatively, the first proximity sensor 114 and the second proximity sensor 116 are located more centrally with respect to the antennas or the device itself. The inertial sensor 118 can be located at a central location or an off-center location. The proximity sensors and the inertial sensor(s) can be located on a display side, a rear cover side, or an edge of the tablet computing device 100.

Referring back to FIG. 1, the inertial sensor 118 can be used to detect movements and orientations of the tablet computing device 100 in three-dimensional space. One or more inertial sensors 118 can be used to detect X-translations 103 in the x-axis, Y-translations 107 in the y-axis, Z-translations 109 in the z-axis, as well as rotations 117 about the z-axis, rotations 113 about the y-axis, and rotations 111 about the x-axis. The measurements by the one or more inertial sensors 118 can be inputs to the proximity condition checker 165. Various embodiments can have different placements of the first proximity sensor 114 and the second proximity sensor 116, as well as different combinations of proximity sensors than just two.

The display 115 may be any display technology, such as electronic ink (e-ink), liquid crystal display (LCD), transflective LCD, light emitting diodes (LED), laser phosphor displays (LSP), and so forth. The tablet computing device 100 may also include one or more input devices, such as keyboards, buttons, touchpads, or other input mechanisms. Alternatively, the display 115 may be a touch screen.

The proximity condition checker 165 can be implemented as hardware, software, firmware, or any combination thereof. In the following description, the proximity condition checker 165 can be implemented in firmware and executed by a processing device of the tablet computing device 100. In short, the proximity condition checker 165 can be used for detecting recovery from temporary proximity sensor saturation caused by water for SAR compliance purposes. In one embodiment, in response to the tablet computing device 100 powering up and starting to transmit first data at a first transmit power level using the first antenna 110 (or the second antenna 112). The first transmit power level can be a default transmit power level that is a reduced power level. The proximity condition checker 165 determines that the first proximity sensor 114 and the second proximity 116, during a first period, are in a saturation state in which a signal to be measured is larger than a measurement range of the respective proximity sensor. The tablet computing device 100 can continue to transmit the first data at the first transmit power level using the first antenna 110 when the first proximity sensor 114 and the second proximity sensor 116 are each in the saturation state. The proximity condition checker 165 detects a first condition where, during a second period, the first proximity sensor is in the saturation state and the second proximity sensor is no longer in the saturation state and, during a third period, the second proximity sensor is in the saturation state and the first proximity sensor is no longer in the saturation state. The second and third periods may be after the first period. This first condition may be indicative of a recovery from temporary proximity sensor saturation caused by water due to the independent transitions of the first proximity sensor and the second proximity sensors between being in the saturation state and not being in the saturation state. Subsequent to detecting the first condition, proximity condition checker 165 can detect a second condition where a user is not proximate to the first proximity sensor 114 or the second proximity sensor 116. In response to detecting the second condition, the tablet computing device 100 transmits third at a second transmit power level using the first antenna 110, the second transmit power level being greater than the first transmit power level.

In a further embodiment, subsequent to detecting the first condition, the proximity condition checker 165 detects a third condition where a user is proximate to the first proximity sensor 114 and is not proximate to the second proximity sensor 116. In response to the detecting the third condition, the tablet computing device 100 can transmit fourth data at the second transmit power level using the second antenna 112. Similarly, if transmitting with the second antenna 112 and the user is proximate to the second proximity sensor 116, the tablet computing device 100 can detect this condition and switch to transmit with the first antenna 110 using the proximity condition checker 165.

In another embodiment, subsequent to detecting the second condition described above, the proximity condition checker 165 can determine that a first value output by the first proximity sensor 114 exceeds a first antenna-switching threshold value and that a second value output by the second proximity sensor 116 exceeds a second antenna-switching threshold value. The proximity condition checker 165 determines an orientation of the tablet computing device 100 using the inertial sensor 118. The proximity condition checker 165 selects the first antenna 110 when the orientation is a first orientation and selects the second antenna 112 when the orientation is a second orientation.

In another embodiment, the proximity condition checker 165 determines that a first proximity sensor 114 and a second proximity sensor 116 are saturated in an unknown state after a power event. The saturation may be caused at least in part by the presence of water in proximity to the first proximity sensor 114 and the second proximity sensor 116. While the first proximity sensor 114 and the second proximity sensor 116 are in the unknown state, the tablet computing device 100 transmits data at a first transmit power level. The proximity condition checker 165 determines that 1) both the first proximity sensor 114 and the second proximity sensor 116 are no longer saturated and 2) water is no longer in proximity to the first proximity sensor 114 and the second proximity sensor 116. In response to a determination of 1) and 2) by the proximity condition checker 165, the tablet computing device 100 can transmit subsequent data at a second transmit power level using the first antenna 110 (or the second antenna 112), the second transmit power level being greater in magnitude than the first transmit power level. Additional details regarding the operations of the proximity condition checker 165 are described below with respect to FIGS. 2-8 below.

Referring back to FIG. 1, the first antenna 110, the second antenna 112, the first proximity sensor 114, the second proximity sensor 116, and the proximity condition checker 165 are shown in the illustrated embodiment using dashed lines to indicate that these components are not on a surface of the tablet computing device 100. For example, some of these components can be located on an inside of a back cover. However, in other embodiments, some of these components could be disposed on a surface of the tablet computing device 100.

Note that in one embodiment sensor electrodes are disposed proximate to the antennas to permit a proximity sensor chip to detect when a human body part or phantom is close to the respective antenna per any one of the proximity conditions. This may include detecting one or more distances between the antenna and the human body part or a phantom. When there are more than two or three sensor electrodes, the sensor electrodes may be disposed in in a linear pattern, a square pattern, an elliptical pattern, a checkerboard pattern, or other pattern. The sensor electrodes may be discrete sensor pads (as shown), or may be linear sensor arrays, other sensor arrays, a touch panel, slider sensors, or the like. As shown, the sensor electrodes are disposed near the first antenna 110 and near the second antenna 112. However, additional sensor electrodes may also be disposed at other locations with relation to the antenna(s). When a human body part or phantom is detected near an antenna per the methods 400, 500, 550, 700, and 800, the transmit power level for that antenna may be throttled, including reducing the transmit power level for data transmission when any one of the proximity conditions is met. Alternatively, the transmit power levels for both antennas may be throttled when any one of the proximity conditions is met.

In one embodiment, the sensor electrodes may be disposed on an underside of a non-conductive substrate, which may be a rigid substrate (e.g., a printed circuit board (PCB)) or a flexible substrate (e.g., a polyimide film, polyester film, or polyether ether ketone (PEEK) film). When multiple antennas are used, sensor electrodes 1235 may be positioned proximate to each antenna. In some embodiments, one or more sensor electrodes may be used for proximity conditions for different antennas. For example, a same sensor electrode can be disposed beyond one end of the antenna in a position that is also beyond one end of the antenna 1220. Alternatively, when the user device includes a single antenna, the sensor electrode 1235 may be positioned proximate to the single antenna. In one embodiment, the sensor electrodes may be located 10 mm from an antenna. Alternatively, the sensor electrodes may be disposed at different locations, and may even be disposed gradually further away from the antenna, such as one sensor electrode at 10 mm, another at 15 mm, another at 20 mm, and another at 25 mm, for example. Depending on which of sensor electrodes the proximity sensor detects the presence of a human body part or phantom and/or relative strengths of detection signals obtained, a distance between the human body part (or phantom) and antenna may be determined. These different sensor electrodes may be used for the different combination of thresholds for checking proximity conditions.

The sensor electrodes may also be disposed on inside of the back cover. In other embodiments, the sensor electrodes may alternatively be positioned within the back cover such that they are flush with the outer perimeter of the back cover, protrude outside of the back cover, or recede within the back cover. Some sensor electrodes may also be attached to a front of the non-conductive substrate (e.g., a printed circuit board (PCB)) or to an inside of the front cover. The substrate may be a rigid substrate (e.g. PCB) or a flexible substrate (polyimide, polyester, polyether ether ketone, etc.). The substrate may also have mounted thereon a sensor integrated circuit electrically connected to the sensor electrodes, such as the proximity sensor chip.

In one embodiment, a user's hand or leg may be in contact with the backside of the user device. During transmission of data, antenna emits a radio frequency (RF) field that may be absorbed by the portions of the human body (e.g., by the hand and/or leg). The amounts of power/radiation that may be absorbed from the RF field by the portions of the human body are based on a distance of the human body part or phantom. The power of the RF field drops off at a rate of $1/d^2$, where d is distance from the antenna. Accordingly, the closer a human body part or phantom is to the antenna, the more radiation that may be absorbed. The different body parts may absorb different amounts of radiation, and the sensor electrodes may be used to determine which antenna needs to be reduced per the proximity conditions. For example, the leg may only absorb a nominal amount of radiation from the RF field because of the distance between the antenna and the leg. However, the hand may be close enough to the antenna to possibly absorb elevated amounts of radiation. In this case, if the hand were positioned over one of sensor electrodes, the sensor proximity sensor chip detects the presence of the hand or phantom. In some embodiments, depending on the sensor type, the proximity sensor chip may detect the presence of a human body part or phantom even if the human body part or phantom is not in direct contact with the sensor electrode or not positioned directly over the sensor electrode. For example, capacitive sensors, inductive sensors, optical sensors, ultrasonic sensors, and the like may detect objects that are proximate to, but not touching, the sensor electrodes. If sensor electrodes are positioned across the entire backside 1230 (e.g., in a sensor array), then signals from multiple sensor electrodes can be processed to visualize a size, shape and/or position of a detected object. This may enable the user device to identify whether a detected object is a human body part or phantom, as well as a distance between the human body part or phantom and the antenna.

Upon detection of the hand, the user device may throttle down an output power level used to transmit data via the antenna, may restrict transmission of data entirely, or may reduce a number of scheduled requests used for data transmission. Such throttling or restriction may remain in place until the hand is no longer detected, at which time normal output power levels may be used for the transmission of data. Various embodiments of power throttling may be used.

Figure 2:
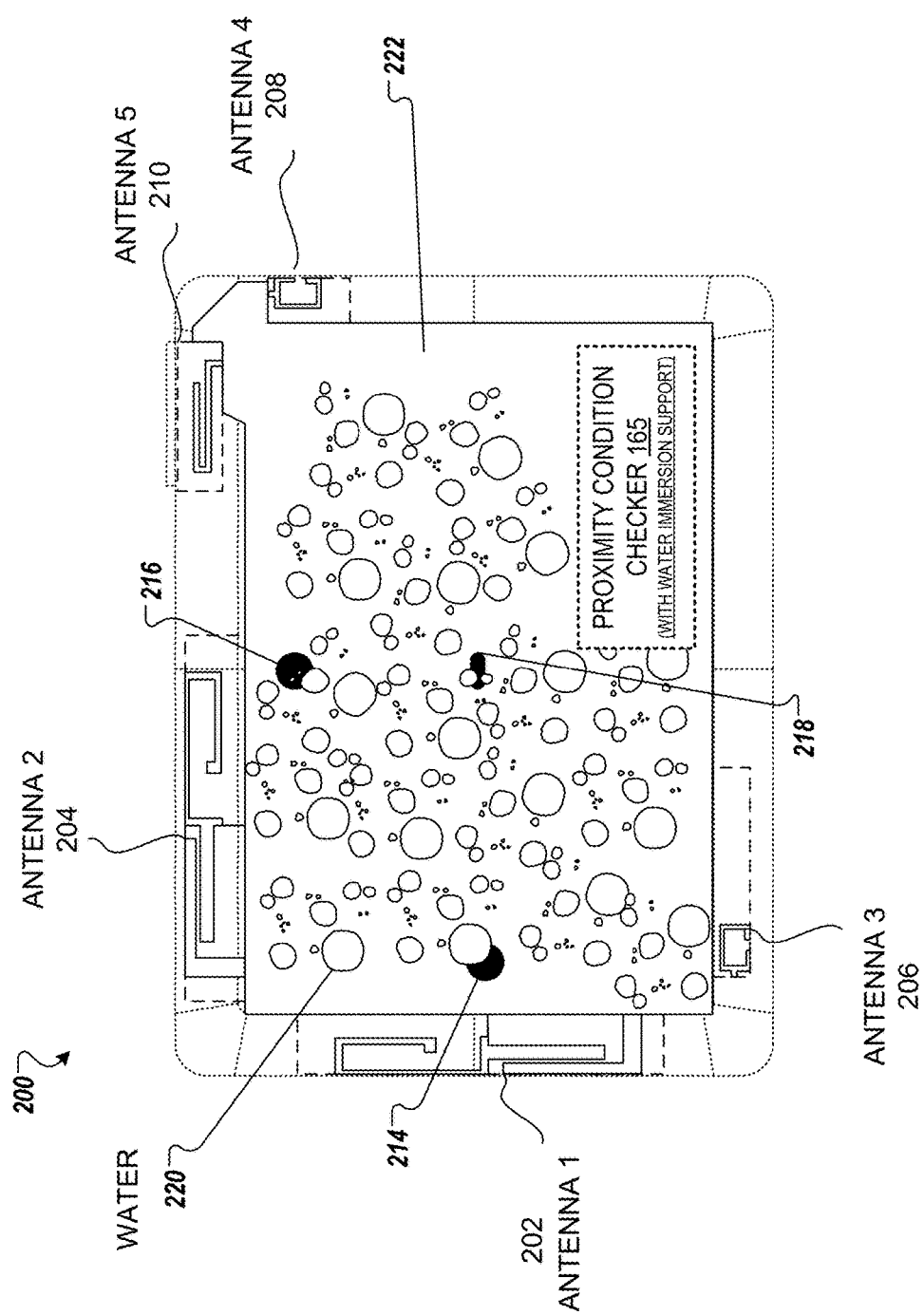
FIG. 2 illustrates a tablet computing device with a proximity condition checker to detect water on a surface of the tablet computing device on or in close proximity to a first proximity sensor and a second proximity sensor according to one embodiment.

FIG. 2 illustrates a tablet computing device 200 with a proximity condition checker 165 to detect water 220 on a surface of the tablet computing device 200 on or in close proximity to a first proximity sensor 214 and a second proximity sensor 216 according to one embodiment. The tablet computing device 200 has a first antenna 202, a second antenna 204, a third antenna 206, a fourth antenna 208, and a fifth antenna 210. In one embodiment, the first antenna 202 and the second antenna 204 are assigned as a primary wireless wide area network (WAN) antenna and a secondary WAN antenna, respectively. The third antenna 206 and the fourth antenna 208 are assigned as a primary wireless local area network (WLAN) antenna and a secondary WLAN antenna, respectively. The fifth antenna 210 is assigned as a global positioning system (GPS) antenna. The tablet computing device 200 also includes a first proximity sensor 214, a second proximity sensor 216, and an inertial sensor 118, similar to those described herein with respect to FIG. 1. Although FIG. 2 illustrates a tablet computing device 200, in other embodiments, other electronic devices may be used in condition with the proximity condition checker 165, as described herein.

FIG. 2 illustrates a backside view of the tablet computing device 200. Water 220 is present on a surface 222 of the tablet computing device 200. The presence of the water 220 impacts operations of the first proximity sensor 214 and the second proximity sensor 216. For example, the tablet computing device 200 may be immersed in water or otherwise subject to water 220. After immersion, the presence of enough water 220 on the surface 222 can cause one or both of the first proximity sensor 214 and the second proximity sensor 216 to be saturated in an unknown state after a power event. The saturation may be caused at least in part by the presence of water 220 in proximity to the first proximity sensor 214, the second proximity sensor 216, or both. While the first proximity sensor 214 and the second proximity sensor 216 are in the unknown state, the tablet computing device 200 can transmit or receive data on any one or more of the antennas 202-210. For SAR compliance, the tablet computing device 200 can initially transmit data at a first transmit power level (as specified reduced power level as a default). Until the proximity condition checker 165 determines that the first proximity sensor 214 and the second proximity sensor 216 have recovered from the proximity sensor saturation state, the tablet computing device 200 transmits data at the first transmit power level. At some point (e.g., even weeks after being immersed in water), the proximity condition checker 165 can determine that 1) both the first proximity sensor 214 and the second proximity sensor 216 are no longer saturated and 2) water 220 is no longer in proximity to the first proximity sensor 214 and the second proximity sensor 216. That is the water 220 is no longer causing saturation of the first proximity sensor 214 and the second proximity sensor 216. In response to a determination of 1) and 2) by the proximity condition checker 165, the tablet computing device 200 can transmit subsequent data at a second transmit power level that is higher than the first transmit power level via any one or more of the antennas 202-210. It should be noted that the proximity condition checker 165 can throttle the transmit power level when there is no user proximate to the tablet computing device 200 according to a power throttling scheme, an antenna switching scheme, or both. That is the proximity condition checker 165 can determine 1) and 2) and that a user is not proximate to the first proximity sensor 214 and the second proximity sensor 216 before throttling the transmit power to the second transmit power level.

To illustrate one specific scenario for SAR compliance, the tablet computing device 200 transmits first data at a first transmit power level using the first antenna 202. The proximity condition checker 165 determines that the first proximity sensor 214 and the second proximity sensor 216 are saturated in an unknown state after a power event. The saturation is caused at least in part by the presence of water 220 in proximity to the first proximity sensor 214 and the second proximity sensor 216. The proximity condition checker 165 determines that 1) both the first proximity sensor 214 and the second proximity sensor 216 are no longer saturated and 2) water 220 is no longer in proximity to the first proximity sensor 214 and the second proximity sensor 216. In response to the determination by the proximity condition checker 165, the tablet computing device 200 transmits second data at a second transmit power level using the first antenna 202; the second transmit power level being greater than the first transmit power level.

In one embodiment, the proximity condition checker 165 determines that the first proximity sensor 214 and the second proximity sensor 216 are saturated by the following: obtaining a first value output by the first proximity sensor 214; obtaining a second value output by the second proximity sensor 216; determining that the first proximity sensor is saturated based on the first value being equal to a maximum value for the first proximity sensor, wherein the maximum value is indicative of the first proximity sensor being in a saturated state; and determining that the first proximity sensor is saturated based on the first value being equal to a maximum value for the first proximity sensor, wherein the maximum value is indicative of the first proximity sensor being in a saturated state. In another embodiment, a difference value between the first value and the second value can be compared against a threshold value to determine whether the first proximity sensor 214 and the second proximity sensor 216 are saturated. Alternatively, the proximity condition checker 165 can determine that the first proximity sensor 214 and the second proximity sensor 216 are saturated using other techniques.

In a further embodiment, to determine that 2) the water 220 is no longer in proximity, the proximity condition checker 165 determines that each the first proximity sensor 214 and the second proximity sensor 216 has not been saturated at the same time as one another since the power event. In another embodiment, to determine 2), the proximity condition checker 165 determines whether there has been a condition after the power event where a first value output by the first proximity sensor 214 and a second value output by the second proximity sensor 216 were below a first saturation threshold and a second saturation threshold, respectively, non-simultaneously. The condition is indicative of the recovery of the first proximity sensor 214 and the second proximity sensor 216 from the proximity sensor saturation state. In another embodiment, to determine 2), the proximity condition checker 165 detects a condition where, during a first period, the first proximity sensor 214 is in saturation and the second proximity sensor 216 is not in saturation and, during a second period, the second proximity sensor 216 is in saturation and the first proximity sensor 214 is not in saturation. This condition is also indicative of the recovery from the proximity sensor saturation state.

In a further embodiment, the proximity condition checker 165 detects a second condition where a user is not proximate to the first proximity sensor 214 or the second proximity sensor 216 subsequent to detecting the condition described below (e.g., non-simultaneous periods of non-saturation by the individual proximity sensors).

In another embodiment, in response to a detection a condition where a user is proximate to the first proximity sensor 214 and is not proximate to the second proximity sensor 216, by the proximity condition checker 165, the tablet computing device 200 transmits second data at the second transmit power level using the second antenna 204, instead of the first antenna 202.

In another embodiment, subsequent to the determining that 2) the water 220 is no longer in proximity to the first proximity sensor 214 and the second proximity sensor 216, the proximity condition checker 165 determines that a first value output by the first proximity sensor 214 exceeds a first antenna-switching threshold value and that a second value output by the second proximity sensor 216 exceeds a second antenna-switching threshold value. The first antenna-switching threshold value and the second antenna-switching threshold value are used to determine whether to switch the user device to transmit using a second antenna. The proximity condition checker 165 determines an orientation of the tablet computing device 200 using the inertial sensor 218. The proximity condition checker 165 selects the first antenna 202 when the orientation is a first orientation and selects the second antenna 204 when the orientation is a second orientation that is different than the first orientation. In another embodiment, the processing logic determines that the user device that the user device is in a first portrait orientation where a first end of the user device is higher in elevation than a second end of the user device using an inertial sensor. The processing logic selects the antenna for transmission when the user device is in the first portrait orientation (screen up). The processing logic determines that the user device that the user device is in a second portrait orientation where the first end of the user device is lower in elevation than the second end of the user device using the inertial sensor. The processing logic selects the second antenna for transmission when the user device is in the second portrait orientation (screen down).

In another embodiment, subsequent to the determining that 2) the water 220 is no longer in proximity to the first proximity sensor 214 and the second proximity sensor 216, the proximity condition checker 165 determines that a first value output by the first proximity sensor 214 exceeds a first antenna-switching threshold value and is greater than a second value output by the second proximity sensor 216. The proximity condition checker 165 selects the second antenna 204 to transmit third data. In response, the tablet computing device 200 transmits the third data at the second transmit power level using the second antenna 204.

In another embodiment, subsequent to the determining that 2) the water 220 is no longer in proximity to the first proximity sensor 214 and the second proximity sensor 216, the proximity condition checker 165 determines that a second value output by the second proximity sensor 216 exceeds a second antenna-switching threshold value and is greater than a first value output by the first proximity sensor 214. In response, the tablet computing device 200 transmits the third data at the second transmit power level using the first antenna 202. It should be noted that in this embodiment, the proximity condition checker 165 does not switch to the second antenna 204 like in the previous embodiment described above.

In a further embodiment, the proximity condition checker 165 determines that 3) either the first proximity sensor 214 or the second proximity sensor 216 is still saturated or 4) water 220 is still in proximity to the first proximity sensor 214 or the second proximity sensor 216. In response to the determination of 3) or 4) by the proximity condition checker 165, the tablet computing device 200 transmits the subsequent data at the first transmit power level using the first antenna 202. Alternatively, the tablet computing device 200 transmits the subsequent data at the first transmit power level using the second antenna 204.

It should be noted that various embodiments above were described with respect to reducing and increasing the transmit power level of the first antenna 202 and switching between the first antenna 202 and the second antenna 204. In other embodiments, the proximity condition checker 165 can determine the conditions described above with respect to any one or more of the first antenna 202, second antenna 204, third antenna 206, fourth antenna 208, and fifth antenna 210. Similarly, the proximity condition checker 165 can switch between different combinations of the antennas, such as switching between transmitting data via the third antenna 206 and the fourth antenna 208 for WLAN communications. Additional details regarding the operations of the proximity condition checker 165 are described below with respect to FIGS. 3-8 below.

Figure 3:
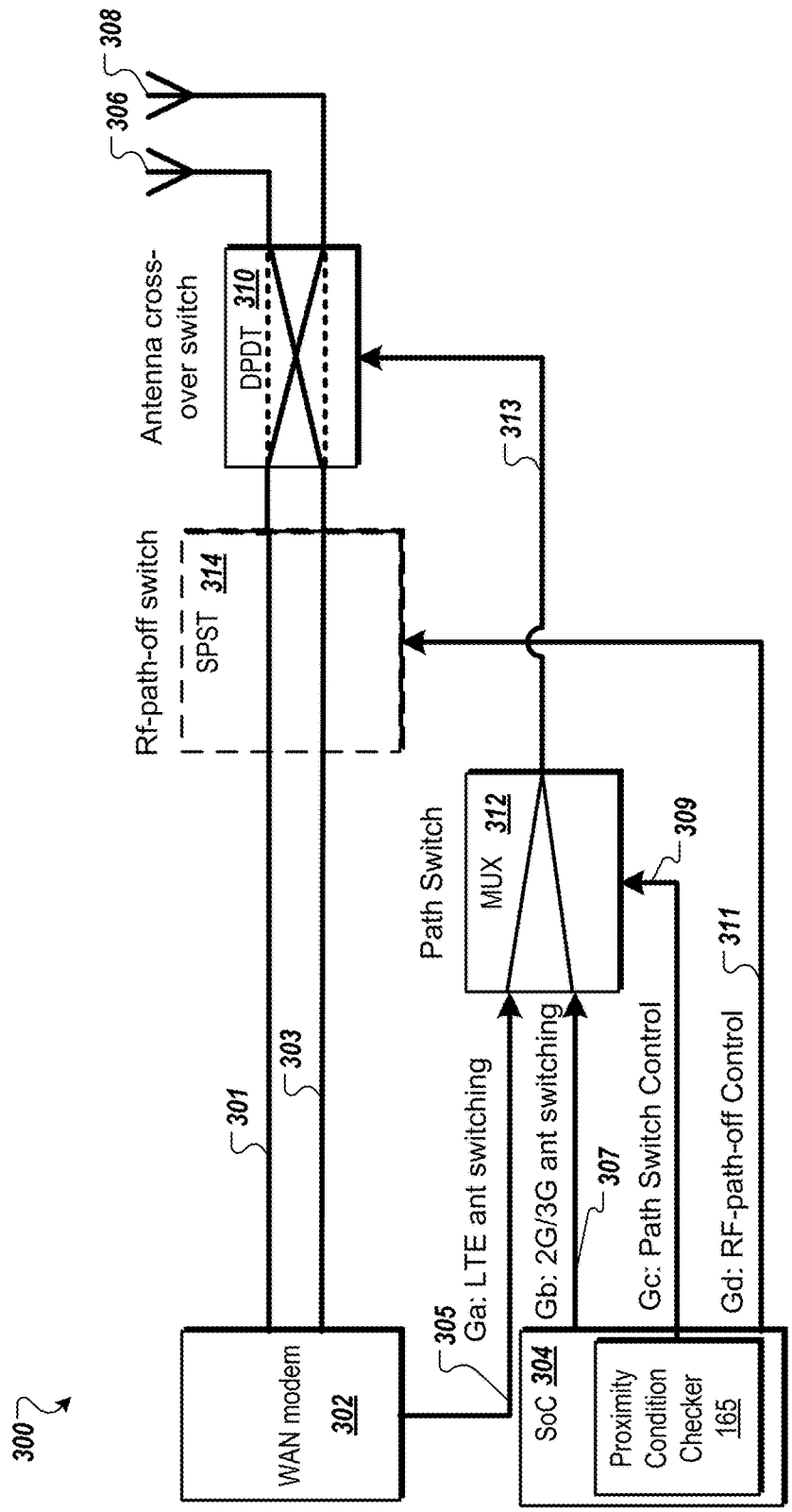
FIG. 3 is a block diagram of an electronic device with a WAN modem and a System on Chip (SoC) with a proximity condition checker according to one embodiment.

FIG. 3 is a block diagram of an electronic device 300 with a WAN modem 302 and a System on Chip (SoC) 304 with a proximity condition checker 165 according to one embodiment. The electronic device 300 has a WAN modem 302 with a first port to output a first TX signal 301 and a second port to output a second TX signal 303. The WAN modem 302 also outputs an antenna switching signal 305. The SoC 304 outputs an antenna switching signal 307, a path switch control signal 309, and an optional RF-path-off control signal 311. The electronic device 300 includes an antenna cross-over switch 310, a path switch 312, and an optional RF-path-off switch 314. The path switch 312 may be a multiplexer with input ports coupled to receive the antenna switching signal 305 from the WAN modem 302 and the antenna switching signal 307 from the SoC 304. The path switch 312 is controlled by the path switch control signal 309 from the SoC 309. The path switch 312 outputs an antenna-cross-over control signal 313 to the antenna cross-over switch 310. The antenna cross-over switch 310 receives both the first TX signal 301 and the second TX signal 303 and selects which of these signals is to be transmitted via the first antenna 306 and which of these signals is to be transmitted via the second antenna 308. The RF-path-off switch 314 receives both the first TX signal 301 and the second TX signal 303 from the WAN modem 302. In response to the RF-path-off control signal 311 from the SoC 304, the RF-path-off switch 314 passes the first TX signal 301 and the second TX signal 303 to the antenna cross-over switch 310 or prevents the first TX signal 301 and the second TX signal 303 from passing to the antenna cross-over switch 310. This effectively turns off the RF path between the WAN modem 302 and the first and second antennas 306, 308. The proximity condition checker 165 may be hardware, software, firmware, or any combination thereof in the SoC 304 to determine based on the proximity sensors which control signals to send to the path switch 312, the antenna cross-over switch 310, and the RF-path-off switch 314.

The following description includes a control flow of these devices and control signals. The WAN modem 302 can start in an off state, and when the WAN modem 302 transitions to an on state, the SoC 304 can give control to the WAN modem 302 and output the following signals on general-purpose input-output (GPIO) terminals: 1) the antenna switching signal 307 is output to select primary antenna A (e.g., first antenna 306); 2) the path switch control signal 309 to select the WAN modem 302, allowing the antenna switching signal 305 to be selected as the antenna-cross-over control signal 313 to control the antenna cross-over switch 310; and 3) the RF-path-off control signal 311 to turn the RF path on. The SoC 304 can give antenna switching control to the WAN modem 302 until the WAN modem 302 is successfully registered (+CREG, +CGREG). After power on registration, the SoC 340 can follow 2G/3G control or LTE control scenarios as set forth below. The SoC 304 may start the proximity condition checker 165, such as starting a processing thread for the power back off, antenna switching. The processing thread sets a SAR state to be ON initially by default. This means the TX power level is set to a reduced transmit power level. The proximity sensor state and the SAR states can be set to an initial unknown state. The SoC 304 can then determine a registration status using registration identifiers (e.g., +CREG and +CGREG in 3GPP specification), indicating that the WAN modem 302 is successfully registered. For example, the SoC 340 can use the following to determine a change in RAT using changes in the registration identifiers.

Once registration status is confirmed, the SoC 304 can determine a current radio access technology (RAT) state and a change in the RAT state. For RAT change detection, the SoC 304 can If the SoC 304 determines that the WAN modem 302 is using LTE technology, the SoC 304 can output the following signals in a control sequence as follows: 1) the RF-path-off control signal 311 to turn the RF path off; 2) the path switch control signal 309 to switch the path to the WAN modem 302 (allowing the antenna switching signal 305 to be selected as the antenna-cross-over control signal 313 to control the antenna cross-over switch 310); and 3) the RF-path-off control signal 311 to turn the RF path on. In one embodiment, the LTE control sequence for a RAT change from 2G/3G to LTE can be as follows:

The sequence for RAT change from 2G/3G to LTE:
Gd—RF-path-off
Gc—Path switch to WAN modem
Gd—RF path on
Subsequent LTE control
Sequence: none (controlled by BAS)

In one embodiment, the LTE control sequence for subsequent LTE control can be controlled by BAS, so there is no sequence by the SoC 304.

If the SoC 304 determines that the WAN modem 302 is using 2G/3G technology, the SoC 304 can output the following signals in a control sequence as follows: 1) the RF-path-off control signal 311 to turn the RF path off; 2) the path switch control signal 309 to switch the path to the SoC 340 (allowing the antenna switching signal 309 to be selected as the antenna-cross-over control signal 313 to control the antenna cross-over switch 310); the antenna switching signal 307 for antenna switch control of the antenna cross-over switch 310; and 4) the RF-path-off control signal 311 to turn the RF path on. The proximity condition checker 165 can be used to determine the antenna switching to be made by the antenna switching signal 307. In one embodiment, the 2G/3G control sequence for a RAT change from RAT change from LTE to 2G/3G can be as follows:

Sequence for RAT change from LTE to 2G/3G
Gd—RF-path-off
Gc—Path switch to SoC
Gb—2G/3G antenna switch control
Gd—RF path on In one embodiment, the 2G/3G control sequence for subsequent 2G/3G control can be as follows:
Gd—RF-path-off
Gb—2G/3G antenna switch control
Gd—RF path on In one embodiment, the antenna selection can be done by antenna selection logic as described herein. The antenna selection logic can use an antenna selection decision table as shown in the following Table 1.

TABLE 1

| 2G/3G Antenna selection decision table (simplified): | | |
|---|---|---|
| Prox sensor A status | Prox sensor B status | Antenna switching decision |
| Passive | Passive | No change (keep current Antenna) |
| Passive | Active | Switching to Antenna A |
| Active | Passive | Switching to Antenna B |
| Active | Active | No change (keep current Antenna) |

Figure 4:
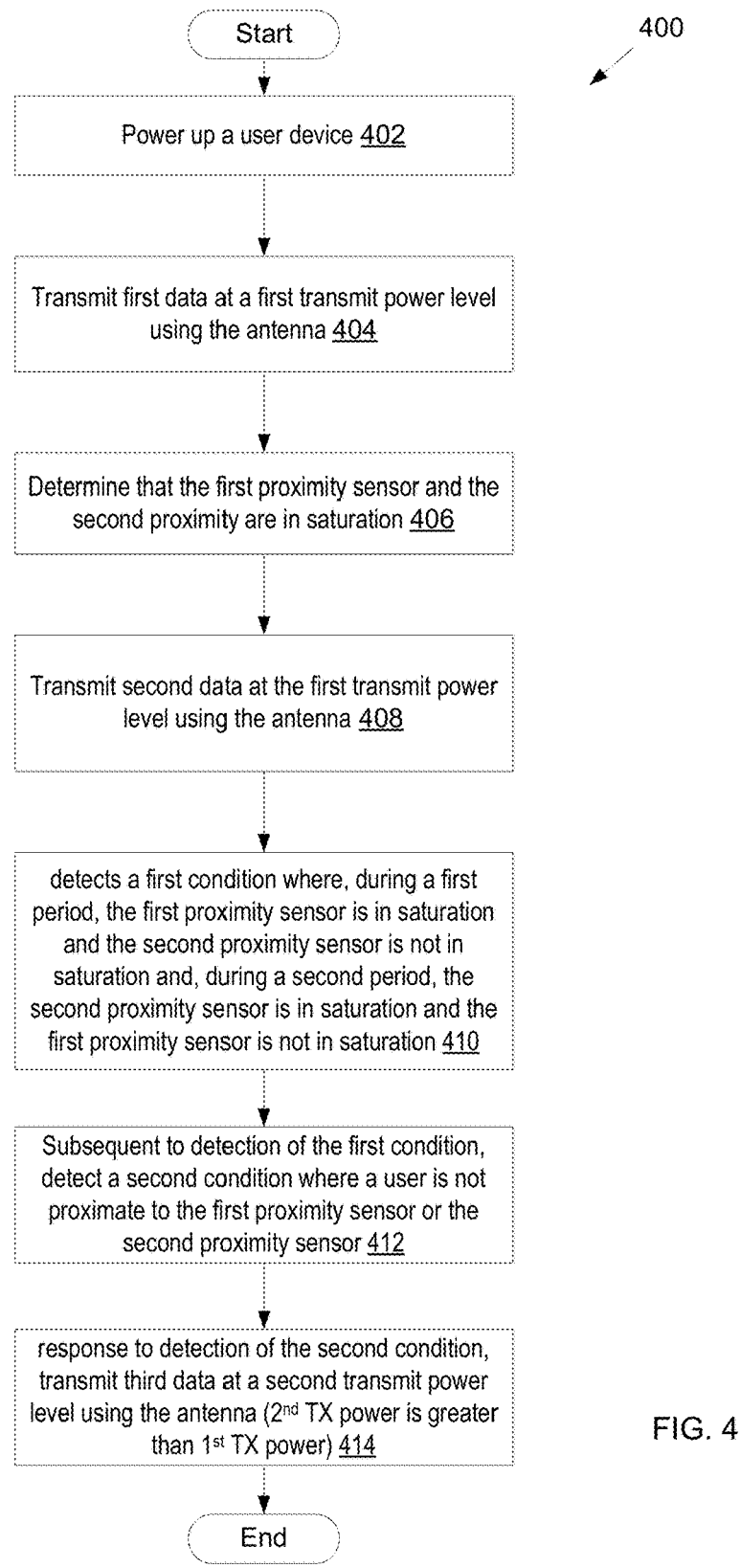
FIG. 4 is a flow diagram of a method for recovery from temporary proximity sensor saturation caused by water for transmit power reduction of a user device for SAR compliance according to one embodiment.
Figure 5A:
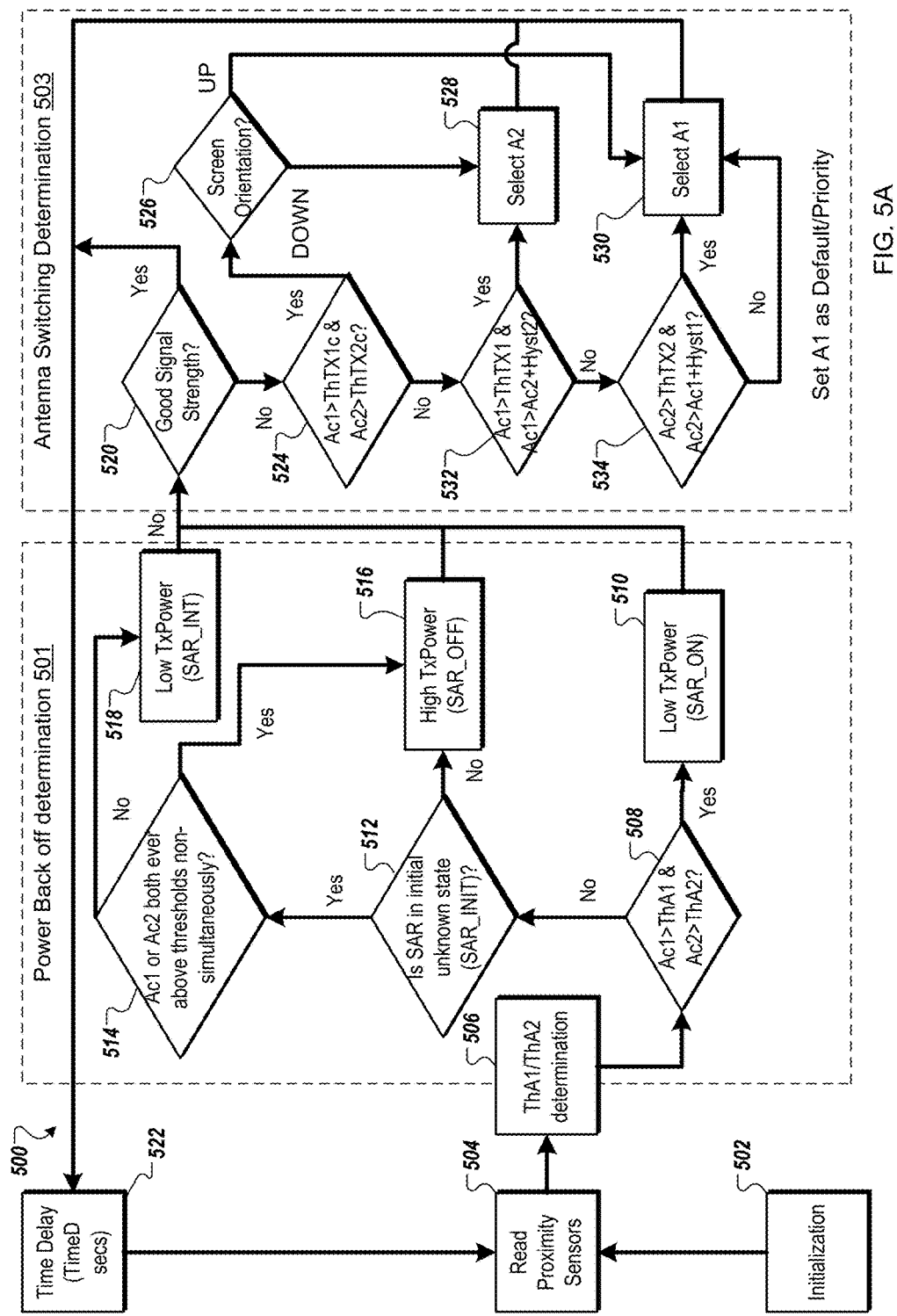
FIG. 5A is a flow diagram of a method for recovery from temporary proximity sensor saturation caused by water for transmit power reduction of a user device for SAR compliance according to another embodiment.
Figure 5B:
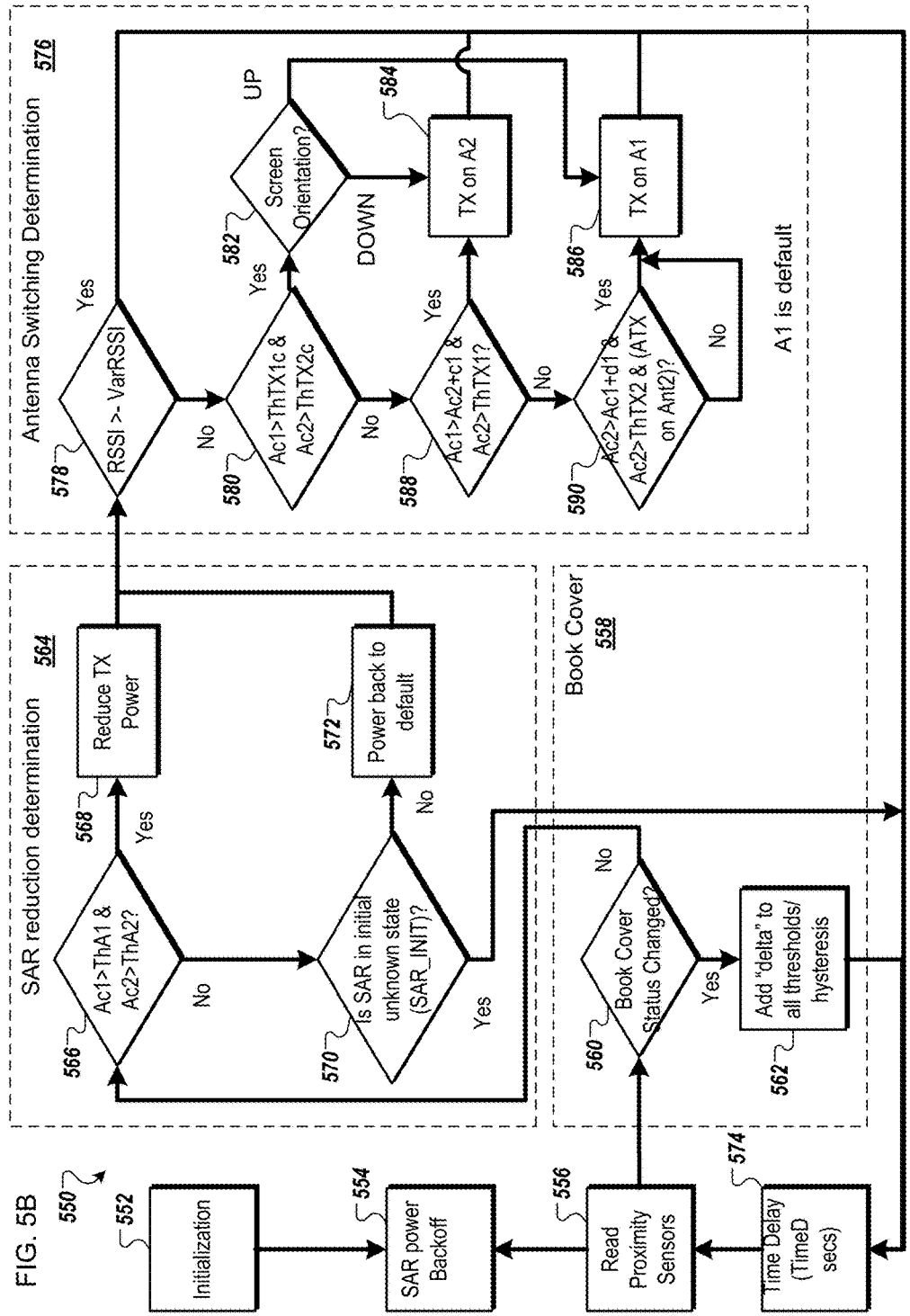
FIG. 5B is a flow diagram of a method for recovery from temporary proximity sensor saturation caused by water for transmit power reduction of a user device for SAR compliance according to another embodiment.

** Guard time: apply X secs guard time to prevent too frequent switching (e.g. 5 secs)
** Optional: apply signal strength threshold to reduce antenna switching frequency Alternatively, the antenna selection logic can use other mechanisms to determine the antenna switching signal 307, such as described with respect to FIGS. 4, 5A, and 5B. When the SoC 304 determines that it needs to power off registration, the SoC 304 can freeze the GPIO control of the antenna cross-over switch 310, the path switch 312, and the RF-path-off switch 314 and turn off the WAN modem 302.

FIG. 4 is a flow diagram of a method 400 for recovery from temporary proximity sensor saturation caused by water for transmit power reduction of a user device for SAR compliance according to one embodiment. Method 400 may be performed by processing logic that may comprise hardware (e.g., circuitry, dedicated logic, programmable logic, microcode, etc.), software (such as instructions running on a processor), firmware, or a combination thereof. In one embodiment, method 400 is performed by tablet computing device 100 of FIG. 1 or tablet computing device 200 of FIG. 2. In another embodiment, the method 400 is performed by the proximity condition checker 165. In another embodiment, the method 400 is performed by a SAR condition checker of a transmit power manager. Alternatively, the proximity sensors 114, 116, the proximity condition checker, or other components of the tablet computing device 100 or 200 can perform some or all of the method 400.

Referring to FIG. 4, the method 400 begins by the processing logic powering up a user device (block 402). The user device includes a first proximity sensor, a second proximity sensor, and an antenna. The processing logic transmits first data at a first transmit power level using the antenna (block 404). At block 406, the processing logic determines that the first proximity sensor and the second proximity sensor are in saturation. In response to the determination at block 406, the processing logic transmits second data at the first transmit power level using the antenna (block 408). The processing logic detects detecting a first condition where, during a first period, the first proximity sensor is in saturation and the second proximity sensor is not in saturation and, during a second period, the second proximity sensor is in saturation and the first proximity sensor is not in saturation (block 410). The first condition is indicative of a recovery from temporary proximity sensor saturation caused by water, as described herein. Another possibility for block 410 is that the first proximity sensor and the second proximity sensor are not in the saturation state at the same time. Subsequent to detecting the first condition, the processing logic detects a second condition where a user is not proximate to the first proximity sensor or the second proximity sensor (block 412). In response to detecting the second condition, the processing logic transmits third data at a second transmit power level using the antenna (block 414), the second transmit power level being greater than the first transmit power level.

In a further embodiment, the processing logic can perform a sensor calibration to obtain baselines measurements (Bx=B1, B2) (also referred to as baseline readings) for the two proximity sensor pads (x=1, 2). That is padx=1 is the first proximity sensor pad 1 and padx=2 is the second proximity sensor pad 2. For the sensor calibration, the processing logic can obtain current measurements (Rx=R1, R2) (also referred to as real time readings) for the two proximity sensor pads and compare them to the respective baseline measurements (Bx=B1, B2) to obtain a difference count (Dx=D1, D2, D3) to calibrate the proximity sensor for each of the proximity sensor pads. For example, the calibration of the proximity sensor can be adjusted until the count difference (Dx) between the baseline measurements (Bx) and the current measurement (Rx) is within two counts. Once the difference counts (Dx) between the baseline measurements (Bx) and the current measurements (Rx) for the three proximity sensor pads (padx) are within two counts, the calibration may be considered complete. Alternatively, other calibration techniques can be used. After calibration, the processing logic can determine if the current measurements indicate a proximity condition is met to increase or reduce the transmit power level.

In another embodiment, the processing logic, subsequent to detecting the first condition, detects a third condition where a user is proximate to the first proximity sensor and is not proximate to the second proximity sensor, the first proximity sensor being located closer to the antenna than a second antenna, the second proximity sensor being located closer to the second antenna than the antenna. In response to detecting the third condition, the processing logic transmits fourth data at the second transmit power level using the second antenna.

In another embodiment, the processing logic, subsequent to detecting the second condition, 1) determines that a first value output by the first proximity sensor exceeds a first antenna-switching threshold value; 2) determines that a second value output by the second proximity sensor exceeds a second antenna-switching threshold value; 3) determines an orientation of the user device using an inertial sensor; and 4) selects the antenna when the orientation is a first orientation or selects the second antenna when the orientation is a second orientation.

In one embodiment, if one or more of the proximity conditions is met, the processing logic puts the user device in a sensor triggered state, a reduced TX power state, an increased TX power state, or the like.

As described herein, the embodiments of the method may define the triggering conditions of a proximity sensor or the triggered state of the user device and the combination of two or more proximity sensors and multiple thresholds can be utilized to determine the triggered and non-triggered states of the user device. It should be noted that the method can be modified to include more proximity conditions and different thresholds than those illustrated and described with respect to depicted embodiments.

In another embodiment, the proximity sensor first conducts a self-calibration to get a baseline reading on each proximity sensor pad. The real time sensor reading generated by each proximity sensor pad can be compared to its own baseline reading. Once the difference is within 2 counts for each sensor, the calibration is considered completed. After the self-calibration is finished, the proximity sensor can enter the checking state where the different triggered and non-triggered conditions are examined repeatedly. For example, the proximity sensor remains in the triggered state if any combination of the conditions is met. A signal may be sent by the proximity sensor to a module to reduce the transmitted power, such as the transmit power manager described herein. Alternatively, the signal can be sent to other modules in a transceiver, a processor, or other processing components that is used for controlling the transmit power level. Once the triggering condition is met, the proximity sensor may stay triggered until different conditions are satisfied. When proximity sensor switches from triggered state to untriggered state, a new self-calibration can be initiated to get a new baseline reading for each sensor pad. It should be noted that these embodiments may be used in user devices that include multiple antennas and corresponding proximity sensor pads located in relation to the multiple antennas. Thresholds can be defined for each of the proximity sensor pads. As described herein, a capacitive type of proximity sensor may have a one-to-one map function where only one threshold can be set for each sensor pad.

FIG. 5A is a flow diagram of a method 500 for recovery from temporary proximity sensor saturation caused by water for transmit power reduction of a user device for SAR compliance according to another embodiment. Method 500 may be performed by processing logic that may comprise hardware (e.g., circuitry, dedicated logic, programmable logic, microcode, etc.), software (such as instructions running on a processor), firmware, or a combination thereof. In one embodiment, method 500 is performed by tablet computing device 100 of FIG. 1 or tablet computing device 200 of FIG. 2. In another embodiment, the method 500 is performed by the proximity condition checker 165. In another embodiment, the method 500 is performed by a SAR condition checker of a transmit power manager. Alternatively, the proximity sensors 114, 116, the proximity condition checker, or other components of the tablet computing device 100 or 200 can perform some or all of the method 500.

Referring to FIG. 5A, the method 500 begins by the processing logic initializing a power back off and antenna switching thread (block 502) to make a power back off determination 501 and an antenna switching determination 503 as set forth below. The processing logic reads the proximity sensors (block 504). The processing logic may receive measurement values from a proximity sensor (circuitry) coupled to the first and second proximity sensor pads (electrodes). Alternatively, the processing logic can access memory locations where the measurement values are stored. Alternatively, the processing logic can measure the measurement values using the first proximity sensor and the second proximity sensor. The term "proximity sensor" may refer to the electrodes and the corresponding measurement circuitry that measure signals in connection with the electrodes. Alternatively, the proximity sensors may refer to just the electrodes depending on the implementation of the algorithm. The sensor reading values at block 504 may include a first measurement Ac1 (also referred to as a sensor reading value) from a first proximity sensor and a second measurement Ac2 from a second proximity sensor. In some implementations, there may be other checks at this point, such as whether there is a book cover state change between no cover, cover closed, cover on the back, cover open, or the like. At this point, an inertial sensor can be read, such as an accelerometer (Tant). This may be used for determining a top antenna (Tant=Ac1 or Ac2).

At block 506, the processing logic can start making key decisions using key decision parameters, such as a threshold determination. In particular, the processing logic can compare the first measurement Ac1 against a first threshold value (ThA1) and the second measurement Ac2 against a second threshold value (ThA2). The first and second threshold values are the values at which power back off occurs. As described below, the first and second measurement values can be compared against other thresholds, such as ThTX1, ThTX2, which are threshold values for the antenna switching determination 503. Also, ThTX1c, ThTX2c are the threshold values used for the antenna switching determination 503 when using an accelerometer. The antenna switching determination 503 can also use hysteresis values, Hyst1, Hyst2, which can be antenna switching hysteresis values that represent a minimum difference between two sensor readings (Ac1, Ac2). The processing logic can also use a time delay at block 522 (TimeD) between sensor readings at block 504. The time delay at block 522 can define a period of power back off determination 501 and antenna switching determination 503.

Referring back to block 506, the processing logic compares the first measurement Ac1 against the first threshold ThA1 and compares the second measurement Ac2 against the second threshold ThA2. The processing logic can check a first condition of the measurements, the first condition being whether the first measurement is greater than the first threshold and the second measurement is greater than the second threshold (e.g., Ac1>ThA1 & Ac2>ThA2) (block 508). If so, the processing logic puts the power back off determination 501 in a low TX power state (SAR_ON) at block 510. In the low TX power state, the processing logic causes the antenna to transmit data at a reduced transmit power level, such as a level to comply with SAR requirements. However, if at block 508, the processing logic determines whether the user device is in an unknown state, caused at least in part by water (block 512). If so, the processing logic determines whether water is no longer in proximity to the first proximity sensor and the second proximity sensor (block 514). In one embodiment, the processing logic makes this determination by determining that each the first proximity sensor and the second proximity sensor has not been saturated at the same time as one another since initialization (block 502), such as in response to a power event of the user device. In another embodiment, the processing logic makes this determination by determining whether there has been a condition after the power event where a first value output by the first proximity sensor and a second value output by the second proximity sensor were below a first saturation threshold and a second saturation threshold, respectively, non-simultaneously, such as illustrated at block 514 in FIG. 5A. If the condition is met, the processing logic puts the user device in a high TX power state (SAR_OFF) (block 516); otherwise, the processing logic puts the user device in an initial known state (SAR_INIT). For example, the user device may stay in the SAR_INIT state until the condition at block 514 occurs. In this manner, the processing logic can detect a recovery from a saturated proximity sensor state to permit the processing logic to switch to the high TX power state at block 516. Whether the processing logic puts the user device in the SAR_ON, SAR_OFF, or SAR_INIT state, the processing logic can transition to the antenna switching determination 503.

Referring to block 520, the processing logic can determine if the signal strength is good, for example, to avoid antenna switching at signal environments that are good enough. In one embodiment, the processing logic may use the latest signal strength reading (e.g., latest RSSI measured). By re-using the values captured for other purposes, such as antenna bar display, the processing logic does not need an additional signal strength query. In another embodiment, the processing logic can perform an additional signal strength query to determine whether the signal strength is good enough according to a specified level. For example, the specified level can be set to a conservative threshold of −80 dBm.

In one embodiment, the antenna switching can be when RSSI is above a good signal threshold. The good signal threshold can be defined relative to the signal strength bars in various technologies. For example, the antenna switching can be enabled when the number of bars is 4 bars or lower, and disabled when the number of bars is 5, such as illustrated in the examples in Table 2-4 as follows:

TABLE 2

2G GSM Signal Bar Thresholds

| RSSI (dBm) | Number of Bars |
|---|---|
| RSSI > −80 | 5 |
| −80 ≥ RSSI > −89 | 4 |
| −89 ≥ RSSI > −98 | 3 |
| −98 ≥ RSSI > −104 | 2 |
| RSSI ≤ −104 | 1 |
| No service | 0 (no service) |

TABLE 3

3G Signal Bar Thresholds

| CPICH RSCP (dBm) | RSCP Bars | CPICH Ec/No (dB) | Ec/No Bars |
|---|---|---|---|
| RSCP > −80 | 5 | Ec/No > −10 | 5 |
| −80 ≥ RSCP > −90 | 4 | −10 ≥ Ec/No > −12 | 4 |
| −90 ≥ RSCP > −100 | 3 | −12 ≥ Ec/No > −14 | 3 |
| −100 ≥ RSCP > −106 | 2 | −14 ≥ Ec/No > −16 | 2 |
| RSCP ≤ −106 | 1 | Ec/No ≤ −16 | 1 |
| No service | 0 (no service) | No service | 0 (no service) |

** Number of Bars to be displayed = minimum of either RSCP Bars or Ec/No Bars

TABLE 4

LTE Signal Bar Thresholds

| RSRP (dBm) | Number of Bars |
|---|---|
| RSRP > −85 | 5 |
| −85 ≥ RSRP > −95 | 4 |
| −95 ≥ RSRP > −105 | 3 |
| −105 ≥ RSRP > −115 | 2 |
| RSRP ≤ −115 | 1 |
| No Sync to LTE Reference Signals | 0 (no service) |

If at block 520 it is determined that the signal strength is good, the processing logic may return to block 522 for the time delay. However, if the signal strength is not good at block 520, the processing logic can perform such additional checks, such as whether the first measurement Ac1 is greater than ThTX1c (first antenna-switching threshold value) and Ac2 is greater than ThTX2c (second antenna-switching threshold value) (block 524). If so, the processing logic can use data from the accelerometer to determine whether to keep a first antenna, A1 (main antenna), transmitting the data or switch to a second antenna (secondary antenna), A2, to transmit the data. For example, the processing logic determines a screen orientation at block 526. If the screen orientation is down, the processing logic selects the second antenna at block 528. If the screen orientation is up, the processing logic selects (or keeps) the first antenna at block 530. In another embodiment, the block 524 is not used when there is no accelerometer. In that case, the processing logic determines whether the first measurement Ac1 is greater than ThTX1 (antenna-switching threshold value) and Ac1 is greater than the second measurement Ac2, plus any optional hysteresis values Hyst2 for Ac2 (block 524). At block 532, the processing logic determines whether the first measurement Ac1 is greater than ThTX1 (first antenna-switching threshold value) and Ac1 is greater than the second measurement Ac2, plus any optional hysteresis values Hyst2 for Ac2. If so, the processing logic selects the second antenna at block 528; otherwise, the processing logic proceeds to block 534. At block 534, the processing logic determines whether the second measurement Ac2 is greater than ThTX2 (second antenna-switching threshold value) and Ac2 is greater than the first measurement Ac1, plus any optional hysteresis values Hyst1 for Ac1. Regardless of the determination, the processing logic selects (or keeps) the first antenna at block 530. In other embodiments, the processing logic does not perform the check at 534 and, based on the outcome of block 534, the processing logic selects either the second antenna at block 528 or the first antenna at block 530.

After selecting the second antenna at block 528 or selecting the first antenna at block 530, the processing logic returns to block 522 for the time delay before reading proximity sensors again at block 504.

It should be noted that the various parameters described herein may be configurable. Alternatively, some or all of the various parameters can be predefined and static. It should also be noted that FIG. 5A illustrates one method 500 for detecting recovery from temporary proximity sensor saturation caused by water.

FIG. 5B is a flow diagram of a method 550 for recovery from temporary proximity sensor saturation caused by water for transmit power reduction of a user device for SAR compliance according to another embodiment. Method 550 may be performed by processing logic that may comprise hardware (e.g., circuitry, dedicated logic, programmable logic, microcode, etc.), software (such as instructions running on a processor), firmware, or a combination thereof. In one embodiment, method 550 is performed by tablet computing device 100 of FIG. 1 or tablet computing device 200 of FIG. 2. In another embodiment, the method 550 is performed by the proximity condition checker 165. In another embodiment, the method 550 is performed by a SAR condition checker of a transmit power manager. Alternatively, the proximity sensors 114, 116, the proximity condition checker, or other components of the tablet computing device 100 or 200 can perform some or all of the method 550.

Referring to FIG. 5B, the method 550 begins by the processing logic initializing a power back off and antenna switching thread (block 552) to make SAR reduction determination 564 and an antenna switching determination 576 as set forth below. The processing logic sets the SAR power back off at block 554. The processing logic reads the proximity sensors (block 556). The processing logic may receive measurement values from a proximity sensor (circuitry) coupled to the first and second proximity sensor pads (electrodes). The sensor reading values at block 556 may include a first measurement Ac1 (also referred to as a sensor reading value) from a first proximity sensor and a second measurement Ac2 from a second proximity sensor. In the depicted embodiment, before the SAR reduction determination 564, the processing logic can do a book cover check 558 in which the processing logic determines whether there is a book cover status change (block 560). If so, the processing logic adds a compensation value (delta) to all threshold values and hysteresis values at a return to time delay at block 574. If there is no book cover status change at block 560, the processing logic proceeds to the SAR reduction determination 564 in which the processing logic can compare the first measurement Ac1 against a first threshold value (ThA1) and the second measurement Ac2 against a second threshold value (ThA2) to check for a first condition of the measurements. The first condition may be when the first measurement is greater than the first threshold and the second measurement is greater than the second threshold (e.g., Ac1>ThA1 & Ac2>ThA2) (block 566). If so, the processing logic reduces the TX power in a reduced TX power state (block 568). In one embodiment, the processing logic makes this determination by determining that each the first proximity sensor and the second proximity sensor has not been saturated at the same time as one another since initialization, such as in response to a power event of the user device. In another embodiment, the processing logic makes this determination by determining whether there has been a condition after the power event where a first value output by the first proximity sensor and a second value output by the second proximity sensor were below a first saturation threshold and a second saturation threshold, respectively, non-simultaneously.

If the first condition is not met, the processing logic determines whether the user device is in an unknown state (SAR_INIT), caused at least in part by water (block 570). If so, the processing logic returns to the time delay at block 574. However, if the user device is not in the unknown state at block 570, the processing logic puts the power back off to default (block 572). For example, if the processing logic determines that the proximity sensors are no longer saturated and the SAR is not in the unknown state, the processing logic can put the user device in a high TX power state (SAR_OFF) (block 572); otherwise, the processing logic puts the user device in an initial known state (SAR_INIT) (block 568). For example, the user device may stay in the SAR_INIT state until the conditions at block 566 and 570 are met. In this manner, the processing logic can detect a recovery from a saturated proximity sensor state to permit the processing logic to switch to the high TX power state at block 572. Whether the processing logic puts the user device in the SAR_ON, SAR_OFF, or SAR_INIT state, the processing logic can transition to the antenna switching determination 576.

Referring to block 578, the processing logic can determine if the signal strength is good, for example, to avoid antenna switching at signal environments that are good enough. In one embodiment, the processing logic may use the latest signal strength reading (e.g., latest RSSI measured) and compare this value against a threshold RSSI (referred to as VarRSSI). By re-using the values captured for another purposes, such as antenna bar display, the processing logic does not need an additional signal strength query. In another embodiment, the processing logic can perform an additional signal strength query to determine whether the signal strength is good enough according to a specified level. For example, the specified level can be set to a conservative threshold of −80 dBm.

If at block 578 it is determined that the signal strength is good, the processing logic may return to block 574 for the time delay. However, if the signal strength is not good at block 578, the processing logic can perform such additional checks, such as whether the first measurement Ac1 is greater than ThTX1$c$ (first antenna-switching threshold value) and Ac2 is greater than ThTX2$c$ (second antenna-switching threshold value) (block 580). If so, the processing logic can use data from the accelerometer to determine whether to keep transmitting data via a first antenna, A1 (main antenna), or switch to a second antenna (secondary antenna), A2, to transmit the data. For example, the processing logic determines a screen orientation at block 582. If the screen orientation is down, the processing logic selects the second antenna at block 584. If the screen orientation is up, the processing logic selects (or keeps) the first antenna at block 586. It should be noted that in this implementation the screen orientation being "up" means that the user is holding the device in such a way that a predefined top of the device is turned up by the user, whereas the screen orientation being "down" means, the user is holding the device in a way that the orientation of the screen has rotated 180 degrees. In this implementation, the screen up and the screen down orientations are two portrait orientations. It should be noted that in other embodiments, a first orientation may be a portrait orientation and the second orientation may be a landscape orientation. The inertial sensor can be used to provide data to determine the orientation. Alternatively, the inertial sensor can provide supplementary data to be used in connection with the data from the proximity sensor to determine the orientation and how a user is holding the device as described herein. In another embodiment, the block 580 is not used when there is no accelerometer. In that case, the processing logic determines whether the first measurement Ac1 is greater than the second measurement Ac2 plus any optional hysteresis value c1 and the second measurement Ac2 is greater than ThTX1 (block 588). If so, the processing logic transmits data on the second antenna A2 at block 584; otherwise, the processing logic proceeds to block 590. At block 590, the processing logic determines whether the second measurement Ac2 is greater than Ac1 plus any optional hysteresis value d1 and Ac2 is greater than ThTX2 (second antenna-switching threshold value). If so, the processing logic transmits data on the first antenna A1 (block 586). At blocks 584, 586, the processing logic proceeds to block 574 for the time delay before reading proximity sensors again at block 556.

It should be noted that the various parameters described herein may be configurable. Alternatively, some or all of the various parameters can be predefined and static. It should also be noted that FIG. 5B illustrates one method 550 for detecting recovery from temporary proximity sensor saturation caused by water. In another embodiment of the method, a user device transmits first data at a first transmit power level using an antenna of the user device. The processing logic determines that a first proximity sensor and a second proximity sensor are saturated in an unknown state after a power event, the saturation caused at least in part by the presence of water in proximity to the first proximity sensor and the second proximity sensor. The processing logic determines that 1) both the first proximity sensor and the second proximity sensor are no longer saturated and 2) water is no longer in proximity to the first proximity sensor and the second proximity sensor. In response to a determination of 1) and 2), the user device transmits second data at a second transmit power level using the antenna; the second transmit power level being greater than the second.

In a further embodiment, to determine that 2) the water is no longer in proximity to the first proximity sensor and the second proximity sensor, the processing logic determines that each the first proximity sensor and the second proximity sensor has not been saturated at the same time as one another since the power event. In a further embodiment to determine that 2) the water is no longer in proximity to the first proximity sensor and the second proximity sensor the processing logic determines whether there has been a condition after the power event where a first value output by the first proximity sensor and a second value output by the second proximity sensor were below a first saturation threshold and a second saturation threshold, respectively, non-simultaneously.

In a further embodiment to determine that 2) the water is no longer in proximity to the first proximity sensor and the second proximity sensor the processing logic detects a condition where, during a first period, the first proximity sensor is in saturation and the second proximity sensor is not in saturation and, during a second period, the second proximity sensor is in saturation and the first proximity sensor is not in saturation. The first condition may be indicative of a recovery from temporary proximity sensor saturation caused by water.

In a further embodiment to determine that 1) both the first proximity sensor and the second proximity sensor are no longer saturated the processing logic detects a second condition where a user is not proximate to the first proximity sensor or the second proximity sensor subsequent to detecting the condition.

In a further embodiment, the processing logic detects a condition where a user is proximate to the first proximity sensor and is not proximate to the second proximity sensor, the first proximity sensor being located closer to the antenna than a second antenna, the second proximity sensor being located closer to the second antenna than the antenna. In response, the processing logic transmits third data at the second transmit power level using the second antenna.

In another embodiment, subsequent to the determining that 2) the water is no longer in proximity to the first proximity sensor and the second proximity sensor, the processing logic performs the following: a) determining that a first value output by the first proximity sensor exceeds a first antenna-switching threshold value; b) determining that a second value output by the second proximity sensor exceeds a second antenna-switching threshold value; c) determining an orientation of the user device using an inertial sensor; d) selecting the antenna when the orientation is a first orientation; and e) selecting the second antenna when the orientation is a second orientation.

In another embodiment, subsequent to the determining that 2) the water is no longer in proximity to the first proximity sensor and the second proximity sensor, the processing logic performs the following: a) determining that a first value output by the first proximity sensor exceeds a first antenna-switching threshold value and is greater than a second value output by the second proximity sensor; b) selecting a second antenna to transmit third data; and c) transmitting, by the user device, the third data at the second transmit power level using the second antenna.

In a further embodiment, subsequent to the determining that 2) the water is no longer in proximity to the first proximity sensor and the second proximity sensor, the processing logic performs the following: a) determining that a second value output by the second proximity sensor exceeds a second antenna-switching threshold value and is greater than a first value output by the first proximity sensor; and b) transmitting, by the user device, third data at the second transmit power level using the antenna.

In one embodiment to determine that the first proximity sensor and the second proximity sensor are saturated, the processing logic measures a first measurement using the first proximity sensor; measures a second measurement using the second proximity sensor; compares the first measurement against a first saturation threshold to determine that the first proximity sensor is saturated; and compares the second measurement against a second saturation threshold to determine that the second proximity sensor is saturated. It should be noted that the saturation thresholds may be different than the thresholds used for detecting the presence of a human body part (sometimes referred to as a touch threshold). In one embodiment, a first touch threshold is set to a level that is less than the first saturation threshold. The saturation threshold may be the max value that the proximity sensor outputs. In another embodiment, the first touch threshold can be set at the first saturation threshold so that the first touch threshold is the same as the first saturation threshold. The same could be true of a second touch threshold for the second proximity sensor with respect to the second saturation threshold. In one embodiment, the processing logic receives the values of the sensors. In another embodiment, the processing logic instructs the proximity sensors to measure and the measurements are stored in memory that is accessible by the processing logic. In another embodiment, instead of receiving the values of the proximity sensor, the processing logic access memory to read stored measurements made by the proximity sensors.

In another embodiment, the processing logic determines that 3) either the first proximity sensor or the second proximity sensor is still saturated or 4) water is still in proximity to the first proximity sensor or the second proximity sensor, and in response to a determination of 3) or 4), transmits the second data at the first transmit power level using the antenna.

In a further embodiment, the processing logic performs a sensor calibration to obtain baselines measurements (Bx=B1 and B2) (also referred to as baseline readings) for the two proximity sensor pads (x=1 and 2) (block 1152). In one embodiment, the pad1=1 is the first proximity sensor pad 1 and x=2 is the second proximity sensor pad 2. For the sensor calibration, the processing logic can obtain current measurements (Rx=R1 and R2) (also referred to as real time readings) for the two proximity sensor pads and compare them to the respective baseline measurements (Bx=B1, B2) to obtain a difference count (Dx=D1, D2) to calibrate the proximity sensor for each of the proximity sensor pads. For example, the calibration of the proximity sensor can be adjusted until the count difference (Dx) between the baseline measurements (Bx) and the current measurement (Rx) is within two counts. Once the difference counts (Dx) between the baseline measurements (Bx) and the current measurements (Rx) for the two proximity sensor pads (padx) are within two counts, the calibration is considered complete. Alternatively, other calibration techniques can be used.

Figure 6:
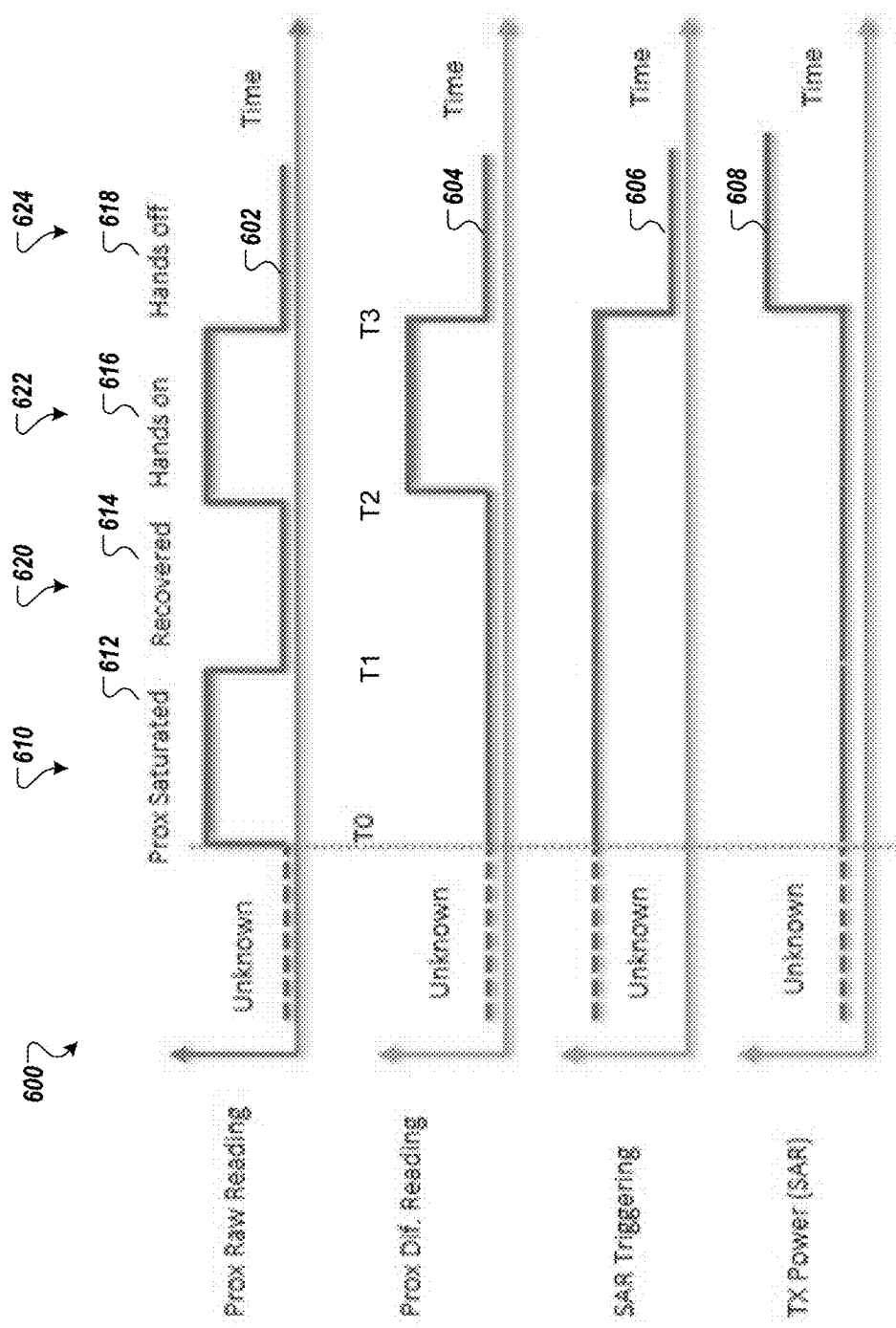
FIG. 6 is a waveform diagram of a power throttling response after recovery from temporary proximity sensor saturation caused by water according to one embodiment.

FIG. 6 is a waveform diagram 600 of a power throttling response after recovery from temporary proximity sensor saturation caused by water according to one embodiment. The waveform diagram 600 includes a first waveform 602 that represents raw proximity sensor readings over time, a second waveform 604 that represents a proximity difference reading between the two proximity sensors, a third waveform 606 that represents a SAR triggering state, and a fourth waveform 608 that represents a TX power (SAR) state. Prior to a first period 610 starting at T0, the raw proximity sensor readings are in an unknown state and at T0 transition the raw proximity sensor readings of the first waveform 602 indicate that the proximity sensors are in a proximity sensor saturation state 612. The proximity sensor saturation state 612 may be caused by the presence of water after water immersion. During a second period 620 starting at T1, the raw proximity sensor readings indicate that the proximity sensors are in a recovered state 614. The proximity sensors may be in the recovered state 614 when the water is removed, evaporates, or is otherwise not in proximity to the proximity sensors. For example, the proximity sensor readings can indicate that a first measurement of the first proximity sensor exceeds a first threshold while a second measurement of the second proximity sensor does not exceed a second threshold, yet later in time, a third measurement of the second proximity sensor exceeds the second threshold, while a fourth measurement of the first proximity sensor does not exceed the first threshold. Alternatively, in the recovered state 614, a first value output by the first proximity sensor and a second value output by the second proximity sensor were determined to be below a first saturation threshold and a second saturation threshold, respectively, non-simultaneously, such as illustrated at block 514 in FIG. 5A. Alternatively, in the recovered state 614, each the first proximity sensor and the second proximity sensor has not been saturated at the same time as one another since initialization (after the proximity sensor saturation state 612).

During a third period 622 starting at T2, the raw proximity sensor readings indicate that the proximity sensors detect the presence of a hand (hands on). As a result, the proximity difference reading indicates a change in state in the second waveform 604. That is one of the proximity sensors may be detected a hand, causing a proximity sensor reading between the two proximity sensors. During the first period 610, the second period 620, and the third period 622, the SAR triggering state remains high and the TX power (SAR) state remains low, given the uncertainty caused by the proximity sensor saturated state 612. However, after the proximity readings indicate that the user device is in a recovered state 614, the TX throttling can be done. However, given the presence of the hand during the third period 622, the SAR trigger state remains high so that the TX power state remains low (transmitting data at a reduced transmit power level). During a fourth period 624, starting at T3, the proximity sensor readings indicate that the hand is no longer proximate to the proximity sensors. The proximity difference reading indicates a change in state in the second waveform 604, the change representing that the hand is no longer proximate to the proximity sensor. As a result, the SAR triggering state in the third waveform 606 transitions to a low state, which causes the TX power (SAR) state to transition to a high state in which the data is transmitted with an increased transmit power level.

It should be noted that in other embodiments, the periods 610, 620, 622, and 624 can occur in different orders, but the SAR triggering state cannot transition to the low state in the third waveform 606 until after the proximity sensors are in the recovered state 614.

Figure 7:
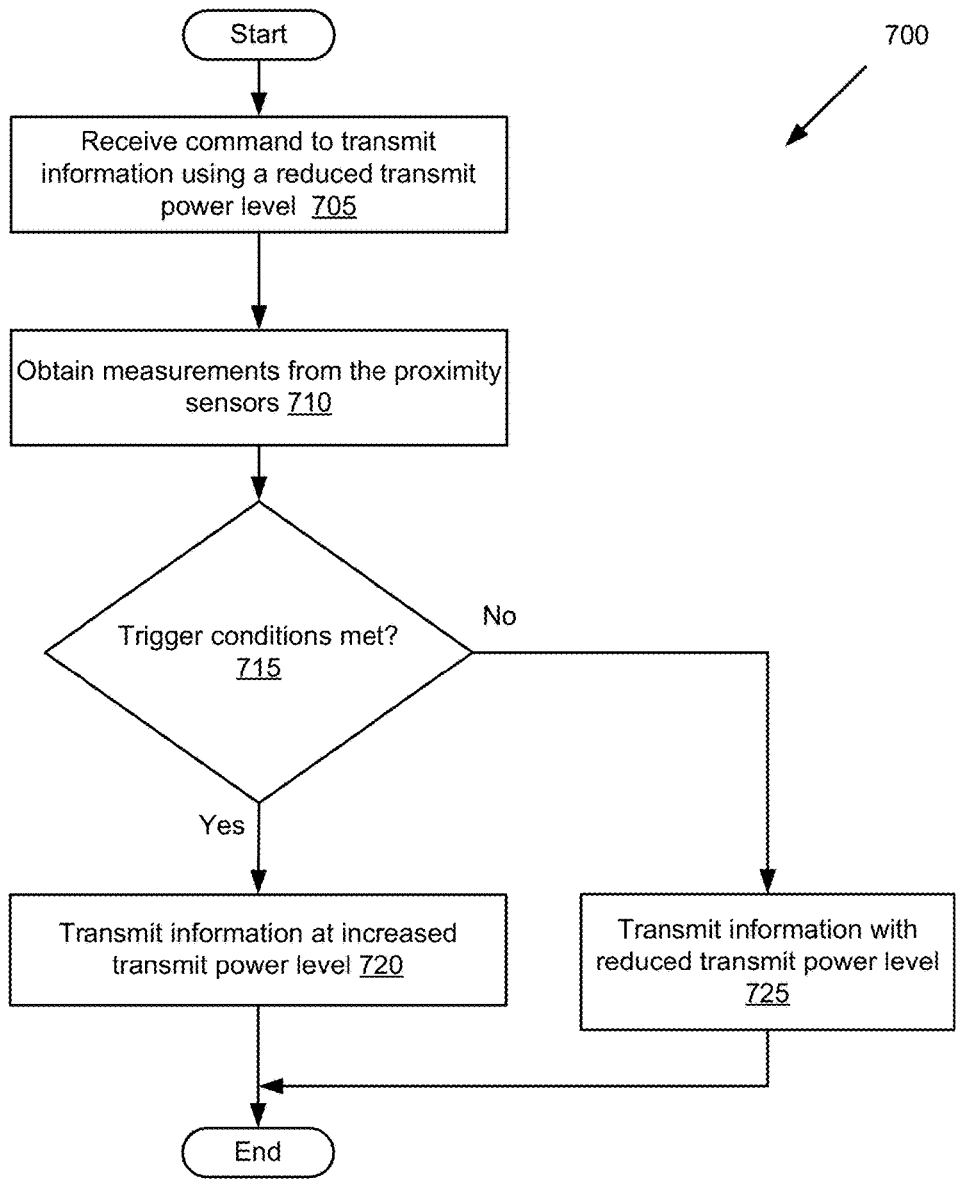
FIG. 7 is a flow diagram of another embodiment of a method for increasing a transmit power level when trigger conditions are met for SAR compliance according to one embodiment.
Figure 8:
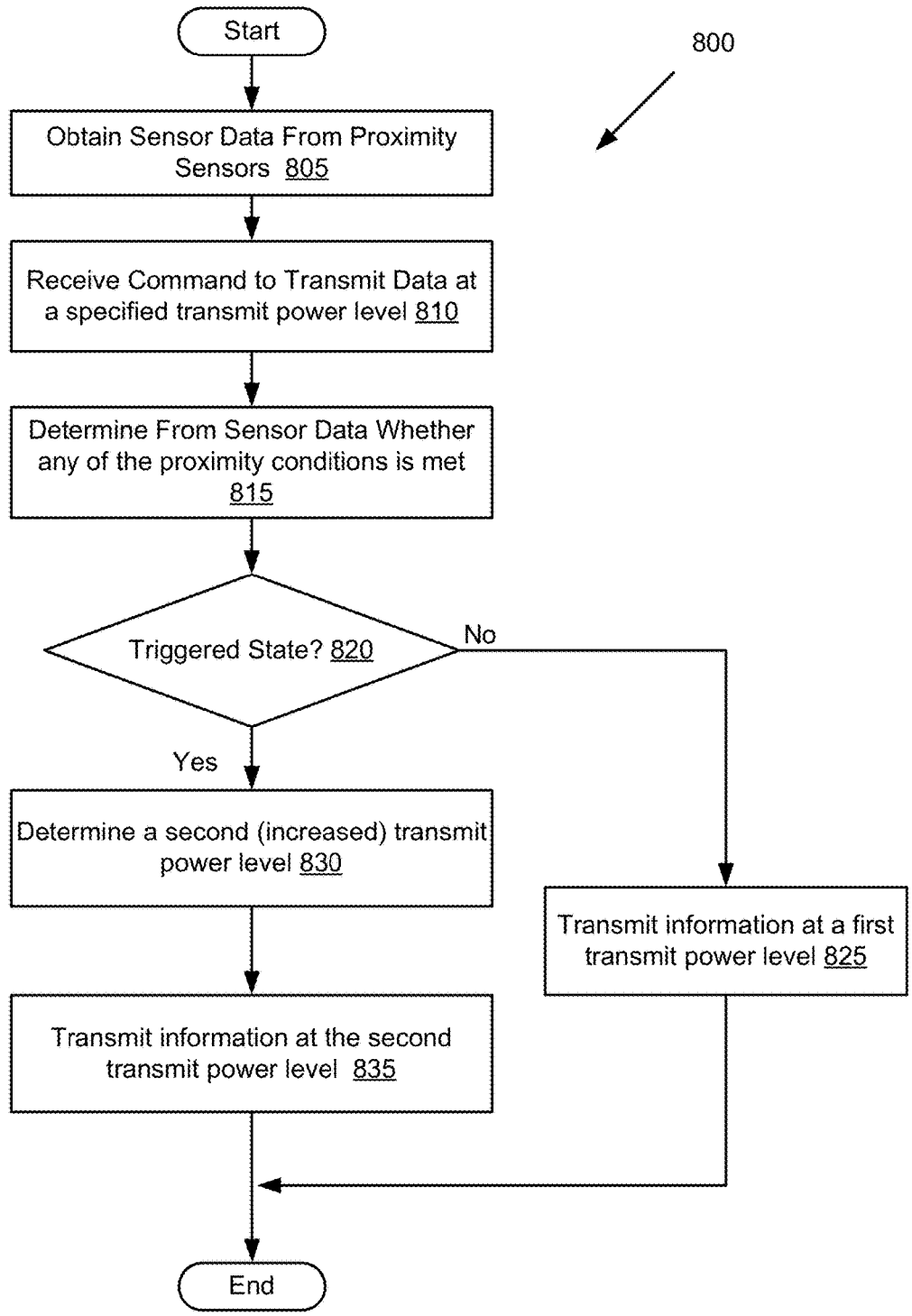
FIG. 8 is a flow diagram of another embodiment of a method for increasing a transmit power level when trigger conditions are met for SAR compliance according to another embodiment.

Method 700 of FIG. 7 and method 800 of FIG. 8 may be performed by processing logic that may comprise hardware (e.g., circuitry, dedicated logic, programmable logic, microcode, etc.), software (such as instructions running on a processor), firmware, or a combination thereof. In one embodiment, methods 700 and 800 are performed by a proximity condition checker 165. In another embodiment, the tablet computing device 100 or 200 perform the methods 700 and 800. In another embodiment, the methods 700 and 800 are performed by the proximity condition checker 165 of the transmit power management 935 of FIG. 9 or transmit power manager 1000 of FIG. 10. In another embodiment, the methods 700 and 800 are performed by the proximity condition checker 165 of the condition checking module 1030 of FIG. 10. Alternatively, other components of the electronic devices described herein may perform some or all of the operations of the methods 700 and 800.

FIG. 7 is a flow diagram of another embodiment of a method 700 for increasing a transmit power level when trigger conditions are met for SAR compliance according to one embodiment. At block 705 of method 700, a command is received to transmit data with a specified transmit power level by a user device. The command may be generated by the user device and the specified transmit power level can be directed by a wireless carrier, a WLAN hotspot, or other wireless communications system. Alternatively, the command may be received from an application running on the user device (e.g., an application for creating a wireless ad hoc network). The user device obtains values of the proximity sensors (block 710). At block 715, the user device determines whether any one of the proximity conditions is met. The proximity conditions include those described above with respect to the proximity condition checker 165 above, such as conditions that indicate that the user device has recovered from a saturated state caused by immersion in water. However, given that the user device is in a default low transmit power state when powering up, the trigger conditions indicate when the transmit power level can be increased while ensuring SAR compliance. If no proximity condition is met, the method 700 proceeds to block 725 to transmit information at the specified transmit power level. If any one of the proximity conditions is met, the method 700 proceeds to block 720.

At block 720, the user device increases the transmit power level to an increased transmit power level and transmits the data at the increased transmit power level. The user device may additionally receive a command to transmit additional data using a different antenna than was used to transmit the original data. Such transmission of the additional data via the additional antenna may also be at the increased power level. The wireless carrier may specify the transmit power level, such as a maximum transmit power level, and the user device may determine a reduced transmit power level for the default state, as well as a power level between the default and the maximum transmit power level for the increased transmit power level. It should be noted that the convention of the trigger conditions may be swapped.

FIG. 8 is a flow diagram of another embodiment of a method for increasing a transmit power level when trigger conditions are met for SAR compliance according to another embodiment. At block 805 of method 800, the user device receives sensor data from the proximity sensors included in a user device to detect an object. The object may be a portion of a human body part or phantom. At block 810, the user device receives a command to transmit data at a specified transmit power level. The user device, however, is in a default transmit power state that transmits at a first transmit power level that is a reduced transmit power level that may be less than the specified transmit power level specified in the command at block 810. At block 815, the user device determines from the sensor data whether any one of the various proximity conditions is met. At block 810, the user device determines if the user device is in a triggered state when any one of the various proximity conditions is met. When the user device is in a triggered state, the method proceeds to block 830 to determine an increased transmit power level and then to block 835 to transmit information at the increased transmit power level. The increased transmit power level can be greater than the reduced transmit power level up to the specified transmit power level specified in the command at block 810. However, if the user device is not in a triggered state at block 820, the method proceeds to block 825 to transmit the data at the first transmit power level (i.e., the reduced transmit power). It should be noted that the convention of a triggered state and an untriggered state may be swapped.

Figure 9:
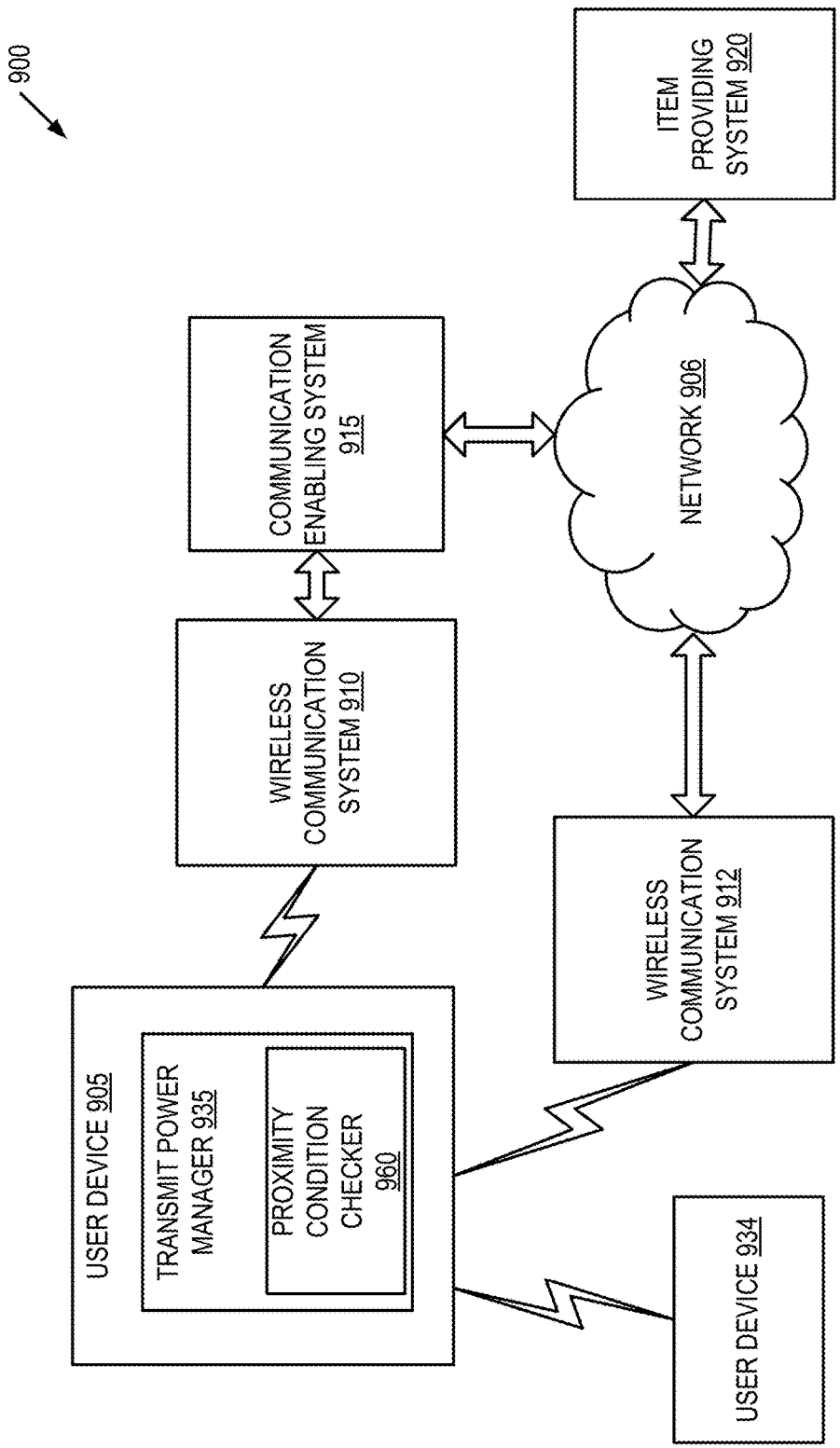
FIG. 9 is a block diagram of an exemplary network architecture in which embodiments of a transmit power manager and a proximity condition checker may operate.

FIG. 9 is a block diagram of an exemplary network architecture 900 in which embodiments of a transmit power manager 935 and a proximity condition checker 165 may operate. The network architecture 900 may include an item providing system 920 and one or more user devices 905 capable of communicating with the item providing system 920 via a network 906 (e.g., a public network such as the Internet or private network such as a local area network (LAN)).

The user devices 905 are variously configured with different functionality to enable consumption of one or more types of media items. The media items may be any type of format of digital content, including, for example, electronic texts (e.g., eBooks, electronic magazines, digital newspapers, etc.), digital audio (e.g., music, audible books, etc.), digital video (e.g., movies, television, short clips, etc.), images (e.g., art, photographs, etc.), and multi-media content. The user devices 905 may include any type of content rendering devices such as electronic book readers, portable digital assistants, mobile phones, laptop computers, portable media players, tablet computers, cameras, video cameras, netbooks, notebooks, desktop computers, gaming consoles, DVD players, media centers, and the like.

The item providing system 920 and the user devices 905 deliver and/or receive items, upgrades, and/or other information via the network 906. For example, the user devices 905 may download or receive items from the item providing system 920. The item providing system 920 also receives various requests, instructions and other data from the user devices 905 via the network 906. The item providing system 920 may include one or more machines (e.g., one or more server computer systems, routers, gateways, etc.) that have processing and storage capabilities to provide the above functionality.

Communication between the item providing system 920 and the user device 905 may be enabled via any communication infrastructure. One example of such an infrastructure includes a combination of a wide area network (WAN) and wireless infrastructure, which allows a user to use the user device 905 to purchase items and consume items without being tethered to the item providing system 920 via hardwired links. The wireless infrastructure may be provided by one or multiple wireless communications systems, such as wireless communications system 910 and wireless communication system 912. One of the wireless communication systems 910, 912 may be a WLAN hotspot connected to the network 906. Another of the wireless communication systems 910, 912 may be a wireless carrier system that can be implemented using various data processing equipment, communication towers, etc. Alternatively, or in addition, the wireless carrier system may rely on satellite technology to exchange information with the user device 905.

The communication infrastructure may also include a communication-enabling system 915 that serves as an intermediary in passing information between the item providing system 920 and the wireless communication system 910. The communication-enabling system 915 may communicate with the wireless communication system 910 (e.g., a wireless carrier) via a dedicated channel, and may communicate with the item providing system 920 via a non-dedicated communication mechanism, e.g., a public Wide Area Network (WAN) such as the Internet.

In one embodiment, while the user device 905 is connected to the wireless communication system 910 and/or wireless communication system 912, one or both of the wireless communication systems periodically or continuously specifies transmit power levels for the user device 905 to use for transmissions to that wireless communication system 910, 912. For example, conventional wireless carrier systems dictate what transmit power levels mobile phones are to use for communications with the wireless carrier systems. The transmit power levels that the wireless carrier systems specify continuously vary based on environmental factors such as a current signal to noise ratio, the distance between the mobile phone and the nearest cell tower, obstacles between the mobile phone and the nearest cell tower, and so on. Conventionally, wireless communication systems consider only signal strength when specifying what transmit power levels the user device is to use in transmissions of data. The user device 905 does take into consideration radiation emitted by the user device 905 that may be absorbed by users of the user device 905, interference with other wireless connections, the battery life of the user device 905, or other factors that may also be important to a user when specifying transmit power levels. Additionally, the user device 905 may have additional information that is not available to the wireless communication systems 910, 912. This additional information may be used to help determine what transmit power levels should be used. For example, the additional information may be whether the user device is in proximity to a human body part or phantom or whether any one of the various proximity conditions is met, and reduce the power accordingly.

In one embodiment, the user device 905 includes a transmit power manager 935 that receives a specified transmit power level from the wireless communication system 910 in response to the declared power level by the user device. The transmit power manager 935 can transmit information at the specified transmit power level or at a reduced transmit power level as described herein. The transmit power manager 935 can also perform its own analysis to determine what transmit power levels should be used for the transmission of data to the wireless communication system 910. For example, the wireless communication system 910 may send a command that the user device is to transmit at a maximum transmit power level, and the transmit power manager 935 instructs the modem when data can be transmitted. During normal operation, the transmit power manager 935 can transmit the data at the maximum transmit power level. When user device 905 detects the presence of a human body part or phantom that meets any one of the various proximity conditions, and, in response, the transmit power manager 935 can reduce the specified transmit power level to a reduced transmit power level for transmission of the data.

In addition to wirelessly connecting to a wireless communication system 910, 912, the user device 905 may also wirelessly connect with other user devices (e.g., user device 905). For example, user device 905 may form a wireless ad hoc (peer-to-peer) network with user device 905. In addition to controlling the transmit power levels used to communicate with the wireless communication systems 910, 912, the transmit power manager 935 may also control the transmit power used to communicate with other user devices 934.

Figure 10:
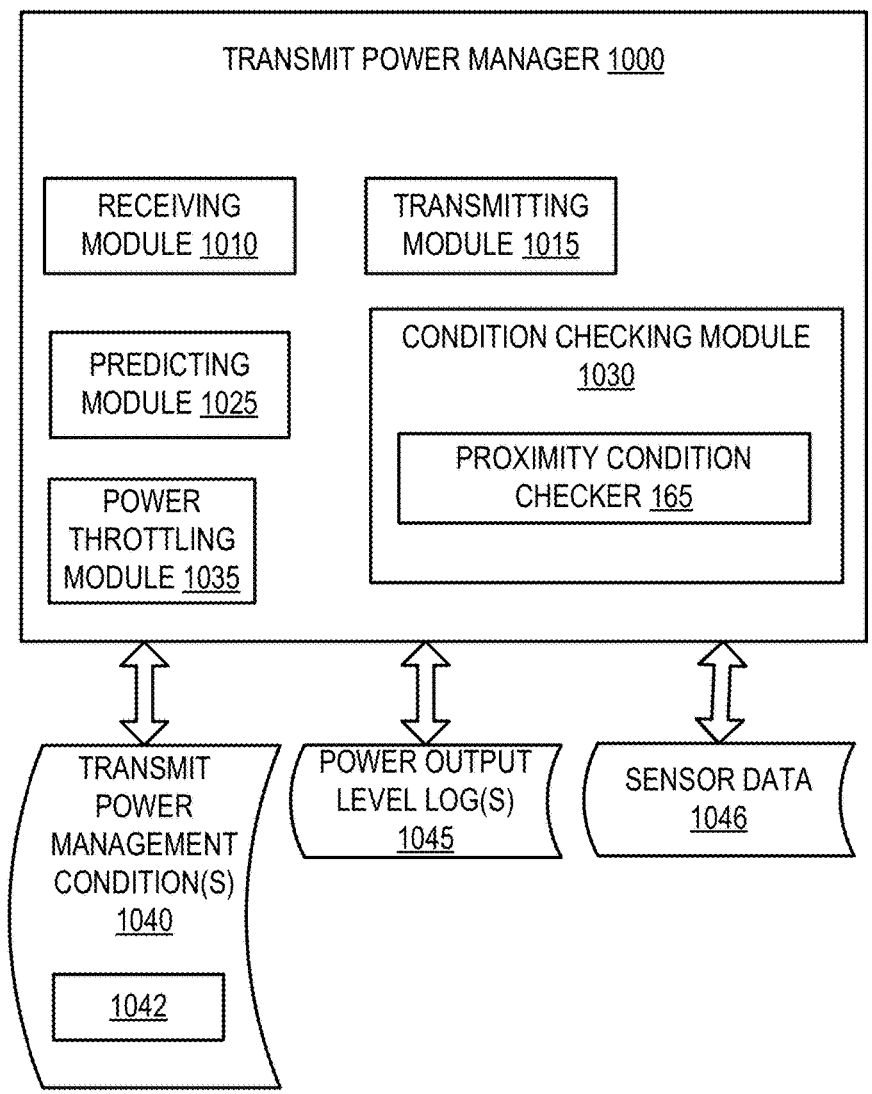
FIG. 10 is a block diagram of one embodiment of a transmit power manager.

FIG. 10 is a block diagram of one embodiment of a transmit power manager 1000, which may correspond to the transmit power manager 935 of FIG. 9. In one embodiment, the transmit power manager 1000 includes a receiving module 1010, a transmitting module 1015, a predicting module 1025, a condition checking module 1030 that includes a proximity condition checker 165, and a power throttling module 1035. The proximity condition checker 1060 can be used to reduce a transmit power level when any one of the various proximity conditions is met as described herein. The receiving module 1010 receives commands to transmit data. The commands to transmit data may identify the specified transmit power level to use for data transmission, for example, the commands may specify that a transmit power level of +33 dbm is to be used), or may specify a current transmit power level as a change from a previously used transmit power level (e.g., an increase of 1 dbm or a decrease of 2 dbm). Commands may also indicate that a previously specified transmit power level should be used. Commands may originate from the wireless communication system and may be routed to the transmit power manager 1000 by a wireless modem and/or processor of the user device. These commands may also be received from other sources, such as applications running on the user device.

Condition checking module 1030 determines whether any transmit power management conditions 1040 apply to transmissions that are to be made. The transmit power management conditions 1040 may include safety conditions, communications interference conditions, battery level conditions, power consumption conditions, and so on. The transmit power management conditions 1040 may apply to communications via a particular wireless communication protocol, with a particular wireless communication system, associated with a particular application, etc. Some transmit power management conditions 1640 may apply to multiple wireless protocols, wireless communications systems, applications, etc. For those transmit power management conditions 1040 that apply to a current transmission, condition checking module 1030 determines whether the conditions will be violated by the current transmission. For example, condition checking module 1030 may determine whether transmit power management conditions will be violated by transmitting data at the specified transmit power level. As described herein, the proximity condition checker 1060 can be used to detect whether any one of the proximity conditions described herein is met to put the user device in a triggered state.

In another embodiment, the transmit power management conditions 1040 include a human body part (or phantom) proximity condition. In another embodiment, the transmit power management conditions 1040 include proximity conditions 1042 that specify the different combination of thresholds needed to test for multiple proximity conditions as described herein. This condition may be violated (or alternatively satisfied) when a human body part or phantom is detected (e.g., when a user is holding the user device), or when a user device determines that a human body part or phantom is closer than a predetermined distance from an antenna of the user device per any of the proximity conditions. In one embodiment, the human body part proximity condition may be determined based on the sensor data 1046. In another embodiment, the transmit power management conditions 1040 may include a user interaction condition that is indicative that a user is currently using the user device to infer that a human body part or phantom is touching or in close proximity to the user device. In one embodiment, the human body part proximity condition or the user interaction condition may be computed by the processor (or other components) and provided as one of the transmit power management conditions 1040 to the transmit power manager 1000. Alternatively, the transmit power manager 1000 may use the sensor data 1046, or other user input data, to determine the human body part proximity condition or the user interaction condition based on the data.

The transmit power management conditions 1040, including the proximity conditions 1042, may include other conditions, such as maximum accumulated transmit power level condition that can be used separately or in combination with some of the other conditions to determine if the condition is violated and to take appropriate action based on the violation. Another example is a communications interference condition for when there are two or more concurrent connections with the different wireless communication system and/or user device. Another example is an active application condition that can be satisfied when a particular application (e.g., an ad hoc network application) is running on the user device or when a particular operation of a specified application is to be performed (e.g., a file transfer operation). Another example is a security condition, such as a maximum transmit distance condition, which may be satisfied when certain applications are active, when certain operations are being performed and/or when certain types of wireless connections are established. The maximum transmit distance condition may cause a transmit power level to be reduced to a level just powerful enough to transmit to nearby devices (e.g., to devices within a range of 6 feet from the user device) in order to increase transmission security by preventing devices outside of a maximum distance from receiving transmissions.

The transmit power management conditions 1040 may be stored in volatile or nonvolatile memory of the user device. In one embodiment, the transmit power management conditions 1040 are hard coded into the user device, and cannot be modified. Alternatively, the transmit power management conditions 1040 may be updated by modifying existing power management conditions, adding new power management conditions, or deleting existing power management conditions.

Returning to FIG. 10, in one embodiment, the transmit power manager 1000 includes a predicting module 1025 that predicts future transmit power levels that may be specified by a wireless communication system. These predictions may be used by the condition checking module 1030 to predict whether transmit power management conditions 1040 are likely to be violated in the future. Some transmit power management conditions 1040 may also incorporate such predicted transmit power levels. For example, violation of some transmit power management conditions 1040 may be contingent upon particular transmit power level predictions. For example, if the user device determines that a maximum accumulated power output level will be reached in the near future, power throttling may begin for current transmissions to prevent such an occurrence.

In one embodiment, the power throttling module 1035 reduces a transmit power level used to transmit data to the wireless carrier system by reducing the specified transmit power level when one or more proximity conditions 1042 have been violated. For example, the power throttling module 1035 can receive an indication from the condition checking module 1030 that any one of the proximity conditions 1042 has been violated, and accordingly, reduce the transmit power level to be used for data transmission. The power throttling module 1035 may also reduce the transmit power level below a specified transmit power level incrementally by incrementally transitioning to lower power classes or by incrementally reducing the number of scheduled requests. In one embodiment, a suitable transmit power level is an output level that does not cause any of the transmission power management conditions to be violated. Alternatively, a suitable transmit power level may be a level that causes the transmission power management condition to stop being violated at some point in the future. For example, a suitable transmit power level may cause a trend towards eventual compliance with the violated transmit power management conditions 1040.

Alternatively, the power throttling module 1035 may compute or otherwise identify a suitable transmit power level, and reduce the current transmit power level to the suitable transmit power level in a single action using the appropriate power class or multi-slot class or by reducing the number of scheduled requests. For example, a transmit power management condition 1040 may specify that any one of the proximity conditions is violated, the transmit power level should be reduced. Alternatively, the transmit power level may be adjusted incrementally until the current transmit power level is at a suitable level.

Power throttling module 1035 may also reduce a duty cycle for the transmissions (e.g., space out the transmissions over time). Therefore, the power throttling module may adjust both the transmit power levels used for transmission and the frequency of those transmissions.

In one embodiment, transmitting module 1015 transmits data to a wireless communication system or additional user device at either a specified transmit power level (e.g., as specified by the wireless communication system) or at a transmit power level determined by the power throttling module 1035. The transmitting module 1015 may transmit the data through one or more antennas included in the user device.

Figure 11:
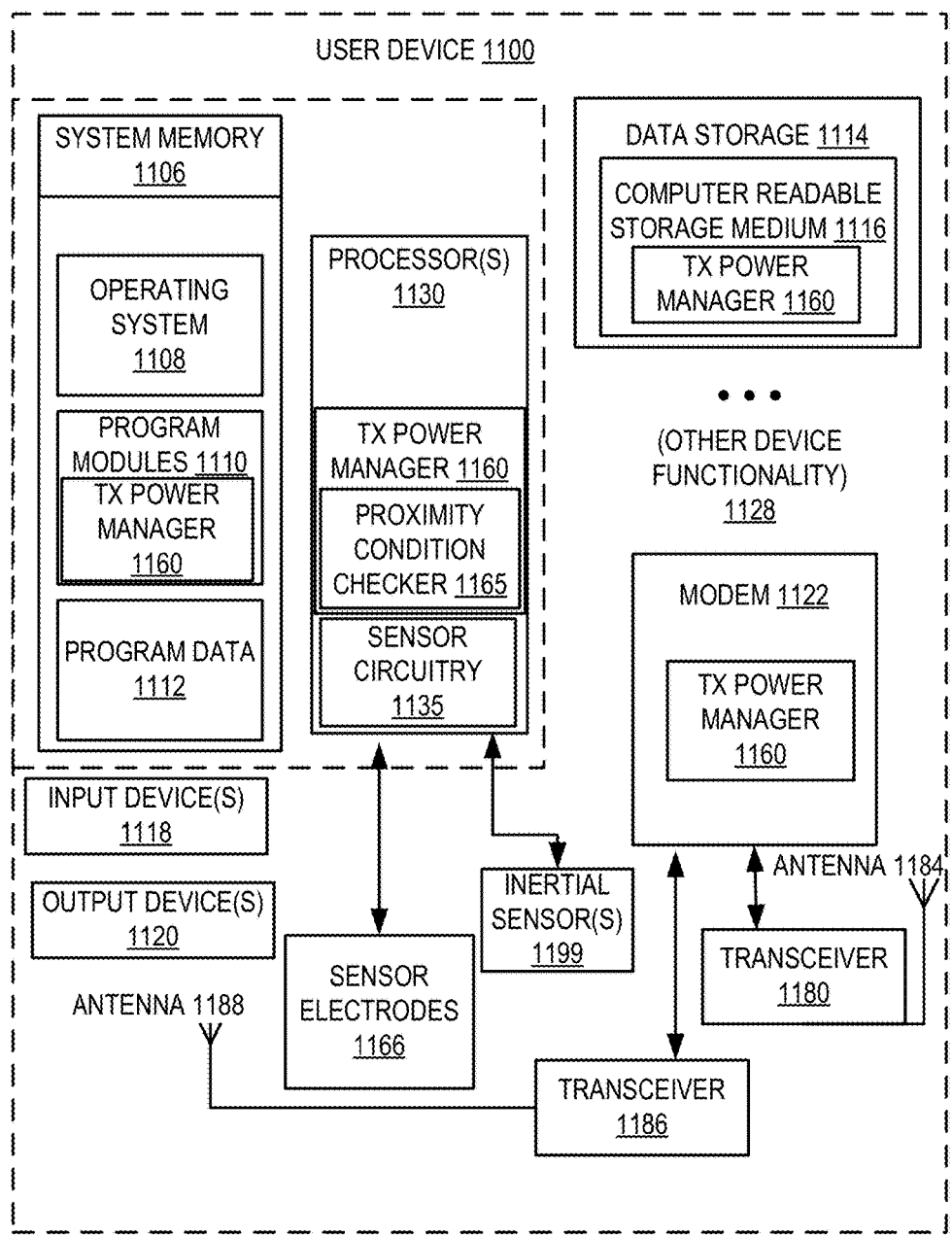
FIG. 11 is a block diagram illustrating one embodiment of an exemplary user device.

FIG. 11 is a block diagram illustrating an exemplary user device 1100. The user device 1100 may correspond to the tablet computing device 100 of FIG. 1, the tablet computing device 200 of FIG. 3, the electronic device 300 of FIG. 3, and may be any type of computing device such as an electronic book reader, a PDA, a mobile phone, a laptop computer, a portable media player, a tablet computer, a camera, a video camera, a netbook, a desktop computer, a gaming console, a DVD player, a computing pad, a media center, and the like.

The user device 1100 includes one or more processors 1130, such as one or more CPUs, microcontrollers, field programmable gate arrays, or other types of processors. The user device 1100 also includes system memory 1106, which may correspond to any combination of volatile and/or non-volatile memory mechanisms. The system memory 1106 stores information that provides an operating system component 1108, various program modules 1110 such as transmit (TX) power manager 1160, including a SAR condition, program data 1112, and/or other components. The user device 1100 performs functions by using the processor(s) 1130 to execute instructions provided by the system memory 1106.

The user device 1100 also includes a data storage device 1114 that may be composed of one or more types of removable storage and/or one or more types of non-removable storage. The data storage device 1114 includes a non-transitory computer-readable storage medium 1116 on which is stored one or more sets of instructions embodying any one or more of the methodologies or functions described herein. The stored instructions, when executed by a processing device, cause the processing device to perform the various operations described herein. As shown, instructions for the transmit power manager 1160 may reside, completely or at least partially, within the computer readable storage medium 1116, system memory 1106 and/or within the processor(s) 1130 during execution thereof by the user device 1100, the system memory 1106 and the processor(s) 1130 also constituting computer-readable media. The user device 1100 may also include one or more input devices 1118 (keyboard, mouse device, specialized selection keys, etc.) and one or more output devices 1120 (displays, printers, audio output mechanisms, etc.).

The user device 1100 further includes a wireless modem 1122 to allow the user device 1100 to communicate via a wireless network (e.g., such as provided by the wireless communication system) with other computing devices, such as remote computers, an item providing system, and so forth. The wireless modem 1122 allows the user device 1100 to handle both voice and non-voice communications (such as communications for text messages, multimedia messages, media downloads, web browsing, etc.) with a wireless communication system (e.g., 1410 or 1412 of FIG. 14). The wireless modem 1122 may provide network connectivity using any type of mobile network technology including, for example, cellular digital packet data (CDPD), general packet radio service (GPRS), EDGE, universal mobile telecommunications system (UMTS), 1 times radio transmission technology (1xRTT), evaluation data optimized (EVDO), high-speed downlink packet access (HSDPA), Wi-Fi, Long Term Evolution (LTE) and LTE Advanced (sometimes generally referred to as 4G), etc. In one embodiment, the wireless modem includes the transmit power manager 1160 in addition to, or instead of, the transmit power manager 1160 being included in the computer readable storage medium 1116, system memory 1106 and/or processor(s) 1130. The transmit power manager 1160 may be implemented as hardware, firmware and/or software of the wireless modem 1122. It should be noted that the modem 1122 may include a processing component that performs various operations to handle both voice and non-voice communications. This processing component can execute the transmit power manager 1160. Alternatively, the transmit power manager 1160 can be executed by a processing component of the user device, such as the processor 1130 or other types of processing devices. In one embodiment, the processor 1130 includes a TX power manager circuit that includes sensor circuitry 1135 to obtain the values of the three or more sensor electrodes 1166 and the functionality of the proximity condition checker 1165 to check the proximity conditions for power throttling.

The wireless modem 1122 may generate signals and send these signals to power transceiver 1180 or transceiver 1186 for amplification, after which they are wirelessly transmitted via antenna 1184 or antenna 1188, respectively. Antenna 1184 and 1188 may be configured to transmit in different frequency bands and/or using different wireless communication protocols. The antennas 1184, 1188 may be directional, omnidirectional, or non-directional antennas. In addition to sending data, antennas 1184, 1188 also receive data, which is sent to wireless modem 1122 and transferred to the processor(s) 1130. The transmit power manager 1160 can instruct the transceiver 1180, 1186 to reduce transmit power levels to be used by the antenna 1134, 1188, respectively.

Though a single modem 1122 is shown to control transmission to both antennas 1184 and 1188, the user device 1100 may alternatively include multiple wireless modems, each of which is configured to transmit data via a different antenna and/or wireless transmission protocol. In one embodiment, each modem includes an independent transmit power manager. Alternatively, a single transmit power manager (e.g., that is included in system memory 1106, processor 1130, and/or data storage 1114) may control transmit power levels used by each wireless modem. In addition, the user device 1100, while illustrated with two antennas 1184, 1188, may include more or fewer antennas in various embodiments.

In one embodiment, user device 1100 includes sensor circuitry 1135 (e.g., a proximity sensor chip) that measures signals on the three or more sensor electrodes 1166. The sensor circuitry 1135 can be a physical contact sensor or a close proximity sensor. The sensor circuitry 1135 can detect the presence of human body parts or phantoms, as well as check the proximity conditions as described herein, and convey information regarding the detected presence and the proximity conditions to the processor(s) 1130. In another embodiment, a proximity sensor chip can be separate from the processor 1130 and the proximity sensor can perform the proximity conditions checks and convey this information to the processor 1130. In another embodiment, the functionality of a proximity sensor chip is implemented in the processor 1130 or on the same IC as a processing component that executes the transmit power manager 1160, such as a modem 1122. In one embodiment, the sensor electrodes 1166 may be capacitive sensor electrodes that are coupled to sensor circuitry 1135 to measure capacitance generated by the presence of the human body part or phantom using any one of various techniques known in the art, for example, relaxation oscillation, a current versus voltage phase shift comparison, resistor-capacitor charge timing, capacitive bridge division, charge transfer, sigma-delta modulation, or charge-accumulation. In an alternative embodiment, the sensors may also be optical (e.g., infrared) sensors that use an emitter and receiver pair to detect the presence of opaque objects. Alternatively, the sensors may be inductive sensors, which include an inductive loop. When the presence of a human body part (or metal object) or phantom is brought close to the inductive sensor element, an induction of the inductive loop changes, causing the human body part or phantom to be detected. Alternatively, the sensors may be ultrasonic sensors that emit an ultrasonic signal and measure a time duration between when a signal is transmitted and the reflection of that signal received (a.k.a., flight response). The sensors may also include other types of sensors, such as those that operate using the detection principles of resistive (e.g., analog resistive, digital resistive or residual resistive), surface acoustic wave, electromagnetic, near field imaging, or other technologies. In one embodiment, multiple different types of sensors are used. Though the detected object is described herein as a human body part or phantom, other types of objects may also be detected depending on the sensing technologies used. The sensor electrodes 1166 may be electrodes used for proximity sensors such as inductive sensors, capacitive sensors, magnetic sensors, infrared sensors, ultrasonic sensors, or the like. The sensor electrodes 1166 may also be used for touch sensors such as a resistive touch sensor, a capacitive touch sensor, a mechanical touch sensor (e.g., a mechanical button), or the like.

In one embodiment, user device 1100 includes one or more inertial sensor electrodes 1199. The inertial sensor electrodes 1199 can be used to detect motion of the user device 1100. In one embodiment, the inertial sensor electrodes 1199 detect linear accelerations (translational movement) and angular accelerations (rotational movement). The inertial sensor electrodes 1199 may include accelerometers and/or gyroscopes. Gyroscopes use principals of angular momentum to detect changes in orientation (e.g., changes in pitch, roll, and twist). Accelerometers measure accelerations along one or more axes (e.g., translational changes). The gyroscope and accelerometer may be separate sensor electrodes or may be combined into a single sensor. The inertial sensor electrodes 1199 in one embodiment are micro-electromechanical systems (MEMS) sensor electrodes. The data from the inertial sensor electrodes 1199 can be used to supplement the values of the proximity sensor electrodes 1166 or to confirm the proximity conditions. The one or more inertial sensors 1199 may have fixed positions within the user device 1100. The gyroscope and accelerometer may be separate sensors or may be combined into a single sensor.

The processor(s) 1130 may include sensor circuitry 1135 (e.g., sensor device drivers) that enables the processor(s) 1130 to interpret signals received from the sensor electrodes 1166 and/or inertial sensor electrodes 1199. In one embodiment, the inertial sensors 1199 output fully processed signals to the processor(s) 1130. Similarly, a proximity sensor that is separate from the processor 1130 can output fully processed signals to the processor 1130 or state signals, such as a triggered state signal, an untriggered state signal, or a state signal with a triggered state or an untriggered state. For example, the proximity sensor may also output a distance, a detected/not detected signal, etc. using a single line interface or a multi-line interface. Similarly, inertial sensors 1199 may output an acceleration value (e.g., in Gs). In another embodiment, the proximity sensor outputs, for example, positional data and/or object presence data (e.g., of a human body part or phantom) to the processors 1130 without first processing the data. Similarly, inertial sensors 1199 may output, for example, voltage values that can be interpreted as acceleration values. In either instance, the processors 1130 may use the sensor circuitry 1135 to process and/or interpret the received data or to measure signals on the sensor electrodes 1166 directly. If data is received from multiple sensors electrodes 1166 and/or inertial sensors 1199, processing the signal may include averaging, identifying a maximum, or other values of the multiple sensor electrodes. In one embodiment, in which the sensors electrodes 1166 are arranged in a sensor array, numerous sensors, or a touch panel, processing the data may include determining where on the user device the human body part or phantom is located from multiple sensor readings.

In the above description, numerous details are set forth. It will be apparent, however, that embodiments of the present invention may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as "inducing," "parasitically inducing," "radiating," "detecting," "determining," "generating," "communicating," "receiving," "disabling," or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the present invention also relate to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein. It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the present invention should, therefore, be determined with reference to the appended claims, along with the full scope of equivalents to which such claims are entitled.

What is claimed is:

1. A method for detecting recovery from temporary proximity sensor saturation caused by water, the method comprising:
    powering up a user device comprising a first proximity sensor, a second proximity sensor, and a first antenna;
    transmitting first data at a first transmit power level using the first antenna;
    determining that, in a first period, the first proximity sensor and the second proximity sensor are each in a saturation state in which a signal to be measured is larger than a measurement range of the respective proximity sensor;
    continuing transmitting the first data at the first transmit power level using the first antenna when the first proximity sensor and the second proximity sensor are each in the saturation state;
    detecting a first condition where, during a second period, the first proximity sensor is in the saturation state and the second proximity sensor is no longer in the saturation state and, during a third period, the second proximity sensor is in the saturation state and the first proximity sensor is no longer in the saturation state, wherein the first condition is indicative of a recovery from temporary proximity sensor saturation caused by water due to the independent transitions of the first proximity sensor and the second proximity sensor between being in the saturation state and not being in the saturation state;
    subsequent to detecting the first condition, detecting a second condition where a user is not proximate to the first proximity sensor or the second proximity sensor; and
    in response to detecting the second condition, transmitting second data at a second transmit power level using the first antenna, the second transmit power level being greater than the first transmit power level.

2. The method of claim 1, further comprising:
    subsequent to detecting the first condition, detecting a third condition where a user is proximate to the first proximity sensor and is not proximate to the second proximity sensor; and
    in response to detecting the third condition, transmitting third data at the second transmit power level using a second antenna that is closer to the second proximity sensor than the first proximity sensor.

3. The method of claim 1, further comprising, subsequent to detecting the second condition:
    determining that a first value output by the first proximity sensor exceeds a first antenna-switching threshold value, wherein the first antenna-switching threshold value is used to determine whether to switch the user device to transmit using a second antenna;
    determining that a second value output by the second proximity sensor exceeds a second antenna-switching threshold value, wherein the second antenna-switching threshold value is used to determine whether to switch the user device to transmit using the second antenna;
    determining that the user device is in a first portrait orientation where a first side of the user device is higher in elevation than a second end of the user device using an inertial sensor;
    using the first antenna to transmit the second data;
    determining that the user device is in a second portrait orientation where the first end is lower in elevation than the second end using the internal sensor; and
    using the second antenna to transmit the second data.

4. A method comprising:
    transmitting, by a user device, first data at a first transmit power level using a first antenna of the user device;
    determining that a first proximity sensor and a second proximity sensor are saturated after a power event, the saturation caused at least in part by presence of water in proximity to the first proximity sensor and the second proximity sensor;
    determining that 1) both the first proximity sensor and the second proximity sensor are no longer saturated and 2) each of the first proximity sensor and the second proximity sensor has not been saturated at a same time as one another since the power event; and
    in response to a determination of 1) and 2), transmitting, by the user device, second data at a second transmit power level using the first antenna, the second transmit power level being greater than the first transmit power level.

5. The method of claim 4, wherein determining that each of the first proximity sensor and the second proximity sensor has not been saturated at the same time as one another since the power event indicates that water is no longer in proximity to the first proximity sensor and the second proximity sensor.

6. The method of claim 4, wherein determining that each of the first proximity sensor and the second proximity sensor has not been saturated at the same time as one another since the power event further comprises determining whether, after the power event, a first value output by the first proximity sensor and a second value output by the second proximity sensor were below a first saturation threshold and a second saturation threshold, respectively, non-simultaneously.

7. The method of claim 4, wherein determining that each of the first proximity sensor and the second proximity sensor has not been saturated at the same time as one another since the power event further comprises detecting, during a first period prior to the determining, that the first proximity sensor is in a saturation state and the second proximity sensor is not in a saturation state and, during a second period prior to the determining, that the second proximity sensor is in the saturation state and the first proximity sensor is not in the saturation state.

8. The method of claim 7, further comprising detecting that a user is not proximate to the first proximity sensor or the second proximity sensor.

9. The method of claim 4, further comprising:
detecting that a user is proximate to the first proximity sensor and is not proximate to the second proximity sensor, the first proximity sensor being located closer to the first antenna than to a second antenna, the second proximity sensor being located closer to the second antenna than to the first antenna; and
transmitting third data at the second transmit power level using the second antenna.

10. The method of claim 4, further comprising, subsequent to the determining that the water is no longer in proximity to the first proximity sensor and the second proximity sensor:
determining that a first value output by the first proximity sensor exceeds a first antenna-switching threshold value;
determining that a second value output the second proximity sensor exceeds a second antenna-switching threshold value;
determining an orientation of the user device using an inertial sensor;
selecting the first antenna when the orientation is a first orientation; and
selecting a second antenna when the orientation is a second orientation.

11. The method of claim 4, further comprising, subsequent to the determining that the water is no longer in proximity to the first proximity sensor and the second proximity sensor:
determining that a first value output by the first proximity sensor exceeds a first antenna-switching threshold value and is greater than a second value output by the second proximity sensor;
and
transmitting, by the user device, third data at the second transmit power level using a second antenna.

12. The method of claim 4, further comprising, subsequent to the determining that the water is no longer in proximity to the first proximity sensor and the second proximity sensor:
determining that a second value output by the second proximity sensor exceeds a second antenna-switching threshold value and is greater than a first value output by the first proximity sensor; and
transmitting, by the user device, third data at the second transmit power level using the first antenna.

13. The method of claim 4, wherein the determining that the first proximity sensor and the second proximity sensor are saturated comprises:
obtaining a first value output by the first proximity sensor;
obtaining a second value output by the second proximity sensor;
determining that the first proximity sensor is saturated based on the first value being equal to a maximum value for the first proximity sensor, wherein the maximum value is indicative of the first proximity sensor being in a saturated state; and
determining that the second proximity sensor is saturated based on the second value being equal to a maximum value for the second proximity sensor, wherein the maximum value for the second proximity sensor is indicative of the second proximity sensor being in a saturated state.

14. The method of claim 4, further comprising:
subsequently determining that either the first proximity sensor or the second proximity sensor is saturated; and
transmitting, by the user device, the second data at the first transmit power level using the first antenna.

15. A non-transitory computer readable storage medium storing instruction that when executed by a processing device cause the processing device to:
cause a first antenna to transmit first data at a first transmit power level;
determine that a first proximity sensor and a second proximity sensor are saturated after a power event, the saturation caused at least in part by the presence of water in proximity to the first proximity sensor and the second proximity sensor;
determine that 1) both the first proximity sensor and the second proximity sensor are no longer saturated and 2) each of the first proximity sensor and the second proximity sensor has not been saturated at a same time as one another since the power event; and
in response to a determination of 1) and 2), cause the first antenna to transmit second data at a second transmit power level, the second transmit power level being greater than the first transmit power level.

16. The non-transitory computer readable storage medium of claim 15, wherein, to determine that each of the first proximity sensor and the second proximity sensor has not been saturated at the same time as one another since the power event, the processing device is further to determine that each of the first proximity sensor and the second proximity sensor has not been saturated at a same time as one another since the power event.

17. The non-transitory computer readable storage medium of claim 15, wherein, to determine that each of the first proximity sensor and the second proximity sensor has not been saturated at the same time as one another since the power event, the processing device is further to determine that the water is no longer in proximity to the first proximity sensor and the second proximity sensor comprises determining whether, after the power event, a first value output by the first proximity sensor and a second value output by the second proximity sensor were below a first saturation threshold and a second saturation threshold, respectively, non-simultaneously.

18. The non-transitory computer readable storage medium of claim 15, wherein, to determine that each of the first proximity sensor and the second proximity sensor has not been saturated at the same time as one another since the power event, the processing device is further to detect, during a first period prior to the processing device determining that each of the first proximity sensor and the second proximity sensor has not been saturated at the same time as one another since the power event, that the first proximity sensor is in a saturation state and the second proximity sensor is not in a saturation state and, during a second period prior to the processing device determining that the water is no longer in proximity, the second proximity sensor is in the saturation state and the first proximity sensor is not in the saturation state.

19. The non-transitory computer readable storage medium of claim 15, wherein the processing device is further to:
detect that a user is proximate to the first proximity sensor and is not proximate to the second proximity sensor, the first proximity sensor being located closer to the first antenna than a second antenna, the second proximity sensor being located closer to the second antenna than the first antenna; and cause the second antenna to transmit third data at the second transmit power level.

20. The non-transitory computer readable storage medium of claim 15, wherein the processing device is further to:
determine that a first value output by the first proximity sensor exceeds a first antenna-switching threshold value;
determine that a second value output by the second proximity sensor exceeds a second antenna-switching threshold value;
determine an orientation of a user device using an inertial sensor, the user device comprising the processing device;
select the first antenna when the orientation is a first orientation; and
select a second antenna when the orientation is a second orientation.

\* \* \* \* \*